United States Patent
Peschke et al.

(10) Patent No.: US 7,186,721 B2
(45) Date of Patent: *Mar. 6, 2007

(54) SUBSTITUTED HEXAHYDROPYRROLO[1,2-A]PYRAZINES, OCTAHYDROPYRIDO[1,2-A]-PYRAZINES AND DECAHYDROPYRAZINO[1,2-A]AZEPINES

(75) Inventors: Bernd Peschke, Malov (DK); Rolf Hohlweg, Kvistgaard (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 11/115,564

(22) Filed: Apr. 27, 2005

(65) Prior Publication Data

US 2005/0267116 A1   Dec. 1, 2005

Related U.S. Application Data

(63) Continuation of application No. 10/453,106, filed on Jun. 3, 2003, now Pat. No. 6,906,060.

(60) Provisional application No. 60/387,047, filed on Jun. 7, 2002.

(30) Foreign Application Priority Data

Jun. 6, 2002   (DK) ................ 2002 00863

(51) Int. Cl.
  *A01N 43/58*   (2006.01)
  *A01N 43/60*   (2006.01)
  *A61K 31/50*   (2006.01)
  *A61K 31/495*  (2006.01)
  *C07D 241/36*  (2006.01)

(52) U.S. Cl. .............. 514/249; 544/238; 544/349

(58) Field of Classification Search .............. None
See application file for complete search history.

(56) References Cited

U.S. PATENT DOCUMENTS 3,164,598 A  1/1965  Freed .................. 260/268
3,388,128 A  6/1968  Day et al. ............. 260/268
6,316,475 B1 11/2001 Bennani et al. .......... 514/343

FOREIGN PATENT DOCUMENTS

| DE | 2029185 | 12/1971 |
|----|---------|---------|
| DE | 2141454 | 3/1972 |
| WO | WO 01/66534 A2 | 9/2001 |
| WO | WO 01/74810 A2 | 10/2001 |

OTHER PUBLICATIONS

Linney et al., Journal of Medicinal Chemistry, vol. 43, pp. 2362-2370 (2000).
DeCosta et al., Journal of Medicinal Chemistry, vol. 36, pp. 2311-2320 (1993).
Bromidge et al., Bioorganic and Medicinal Chemistry Letters, vol. 12, pp. 1357-1360 (2002) 1360 (2002).
Alguacil and Perez-Garcia, "Histamine H3 Receptor: A potential Drug Target for the Treatment of Central Nervous System Disorders" Current Drug Targets—vol. 2(5), pp. 303-313 (Oct. 2003).
Leurs et al., "Therapeutic potential of histamine H3 receptor agonists and antagonists" Trends in Pharmacological Sciences, vol. 19(5), pp. 177-183 (May 1998).

*Primary Examiner*—Zachary C. Tucker
(74) *Attorney, Agent, or Firm*—Rosemarie R. Wilk-Orescan; Reza Green; Richard W. Bosk

(57) ABSTRACT

Novel substituted hexahydropyrrolo[1,2-a]pyrazines, octahydropyrido[1,2-a]-pyrazines and decahydropyrazino [1,2-a]azepines, use of these compounds as pharmaceutical compositions, pharmaceutical compositions comprising the compounds, and a method of treatment employing these compounds and compositions. The compounds show a high and selective binding affinity to the histamine H3 receptor indicating histamine H3 receptor antagonistic, inverse agonistic or agonistic activity. As a result, the compounds are useful for the treatment of diseases and disorders related to the histamine H3 receptor.

5 Claims, No Drawings

SUBSTITUTED HEXAHYDROPYRROLO[1,2-A]PYRAZINES, OCTAHYDROPYRIDO[1,2-A]-PYRAZINES AND DECAHYDROPYRAZINO[1,2-A]AZEPINES

CROSS REFERENCE TO RELATED APPLICATIONS

This application is a continuation of U.S. patent application Ser. No. 10/453,106 filed on Jun. 3, 2003, now U.S. Pat. No. 6,906,060, and claims the benefit of Danish application No. PA 2002 00863 filed on Jun. 6, 2002, and U.S. provisional application No. 60/387,047 filed on Jun. 7, 2002, the disclosure of each of which is hereby incorporated by reference in its entirety.

FIELD OF THE INVENTION

The present invention relates to novel substituted hexahydropyrrolo[1,2-a]pyrazines, octahydropyrido[1,2-a]pyrazines and decahydropyrazino[1,2-a]azepines, to the use of these compounds as pharmaceutical compositions, to pharmaceutical compositions comprising the compounds, and to a method of treatment employing these compounds and compositions. The present compounds show a high and selective binding affinity to the histamine H3 receptor indicating histamine H3 receptor antagonistic, inverse agonistic or agonistic activity. As a result, the compounds are useful for the treatment of diseases and disorders related to the histamine H3 receptor.

BACKGROUND OF THE INVENTION

The existence of the histamine H3 receptor has been known for several years and the receptor is of current interest for the development of new medicaments. Recently, the human histamine H3 receptor has been cloned. The histamine H3 receptor is a presynaptic autoreceptor located both in the central and the peripheral nervous system, the skin and in organs such as the lung, the intestine, probably the spleen and the gastrointestinal tract. Recent evidence suggests that the H3 receptor shows intrinsic, constitutive activity, in vitro as well as in vivo (i.e. it is active in the absence of an agonist. Compounds acting as inverse agonists can inhibit this activity. The histamine H3 receptor has been demonstrated to regulate the release of histamine and also of other neurotransmitters such as serotonin and acetylcholine. A histamine H3 receptor antagonist or inverse agonist would therefore be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists and antagonists could be important mediators of neuronal activity. Accordingly, the histamine H3 receptor is an important target for new therapeutics.

Several publications disclose the preparation and use of histamine H3 agonists and antagonists. Most of these are imidazole derivatives. However, recently some imidazole-free ligands of the histamine H3 receptor have been described (see eg Linney et al., *J. Med. Chem.* 2000, 43, 2362–2370; U.S. Pat. No. 6,316,475, WO 01/66534, WO 01/74810.

In view of the art's interest in histamine H3 receptor agonists, inverse agonists and antagonists, novel compounds which interact with the histamine H3 receptor would be a highly desirable contribution to the art. The present invention provides such a contribution to the art being based on the finding that a novel class of substituted hexahydropyrrolo[1,2-a]pyrazines, octahydropyrido[1,2-a]pyrazines and decahydropyrazino[1,2-a]azepines has a high and specific affinity to and potency at the histamine H3 receptor.

Compounds having a certain similarity to the compounds of the present invention have previously been prepared, and their biological properties have been investigated, cf. Decosta et al., *J. Med. Chem.* 36 (16) 2311–2320 (1993) and Bromidge et al., *Bioorg. Med. Chem. Lett.* 12 (10) 1357–1360 (2002). However, these references do not disclose that these compounds may have a histamine H3 receptor antagonistic or agonistic activity.

Due to their interaction with the histamine H3 receptor, the present compounds are useful in the treatment of a wide range of conditions and disorders in which an interaction with the histamine H3 receptor is beneficial. Thus, the compounds may find use e.g. in the treatment of diseases of the central nervous system, the peripheral nervous system, the cardiovascular system, the pulmonary system, the gastrointestinal system and the endocrinological system.

SUMMARY OF THE INVENTION

The invention relates to a compound of the general formula (I):

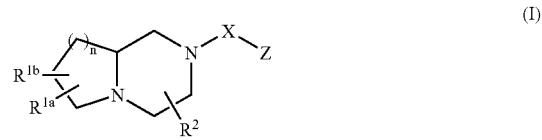

wherein
n is 1, 2 or 3,
$R^{1a}$ and $R^{1b}$ independently are hydrogen, $C_{1-6}$-alkyl, $C_{2-6}$-alkenyl, $C_{2-6}$-alkynyl, $C_{3-8}$-cycloalkyl, $C_{3-8}$-cycloalkenyl or fluoro,
$R^2$ is hydrogen, $C_{1-6}$-alkyl, $C_{2-6}$-alkenyl, $C_{2-6}$-alkynyl, $C_{3-8}$-cycloalkyl or $C_{3-8}$-cycloalkenyl,
X is

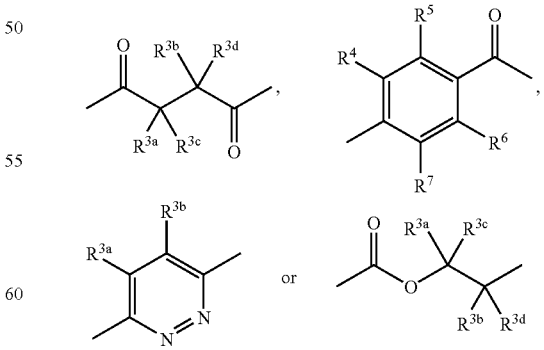

$R^{3a}$, $R^{3b}$, $R^{3c}$ and $R^{3d}$ independently are hydrogen, halogen, $C_{1-6}$-alkyl or $C_{3-8}$-cycloalkyl, or $R^{3a}$ and $R^{3b}$, $R^{3a}$ and $R^{3c}$ or $R^{3c}$ and $R^{3d}$ can be taken together to form a $C_{1-6}$-alkylene bridge, $R^4$, $R^5$, $R^6$ and $R^7$ independently are hydrogen, halogen, $C_{1-6}$alkyl or $C_{3-8}$-cycloalkyl, Z is

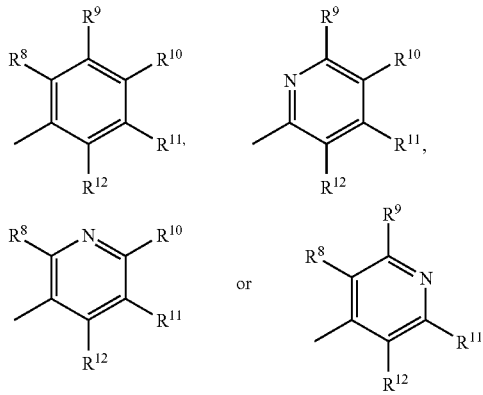

$R^8$, $R^9$, $R^{10}$, $R^{11}$ and $R^{12}$ independently are
  hydrogen, cyano, nitro, halogen, carboxy, guanidino, or amidino,
  $C_{1-6}$-alkyl, $C_{1-6}$-alkoxy, $C_{2-6}$-alkenyl, $C_{2-6}$-alkynyl, $C_{1-6}$-alkylsulfonyl, $C_{1-6}$-alkylsulfinyl, $C_{1-6}$-alkylthio, $C_{1-6}$-alkylcarbonyl, $C_{3-8}$-cycloalkyl, $C_{3-8}$-cycloalkylcarbonyl, $C_{3-8}$-cycloalkenyl, aryl, arylsulfonyl, arylsulfinyl or arylthio,
  each of which may optionally be substituted with one or more groups selected from cyano, nitro, halogen, carboxy, guanidino, amidino, trifluoromethyl, trifluoromethoxy, —$NR^{13}R^{14}$, —$NHC(=O)R^{15}$ or —$C(=O)NR^{13}R^{14}$,
  —$NR^{13}R^{14}$, —$NHC(=O)R^{15}$, —$OC(=O)NR^{13}R^{14}$, —$NHC(=O)OR^{16}$ or —$C(=O)NR^{13}R^{14}$, or $R^8$ and $R^9$, $R^9$ and $R^{10}$, $R^{10}$ and $R^{11}$, or $R^{11}$ and $R^{12}$ can be taken together to form a bridge selected from $C_{1-6}$-alkylene, —O—$(CH_2)_o$—O— and —O—$(CH_2)_o$—, o is 1, 2, 3, 4 or 5, $R^{13}$, $R^{14}$ and $R^{15}$ independently are hydrogen or
aryl, $C_{1-6}$-alkyl, $C_{2-6}$-alkenyl, $C_{2-6}$-alkynyl, $C_{3-8}$-cycloalkyl or $C_{3-8}$-cycloalkenyl, each of which may optionally be substituted with one or more groups selected from cyano, nitro and halogen, $R^{16}$ is
aryl, $C_{1-6}$-alkyl, $C_{2-6}$-alkenyl, $C_{2-6}$-alkynyl, $C_{3-8}$-cycloalkyl or $C_{3-8}$-cycloalkenyl, each of which may optionally be substituted with one or more groups selected from cyano, nitro and halogen, as well as any diastereomer or enantiomer or tautomeric form thereof including mixtures of these or a pharmaceutically acceptable salt thereof.

Definitions

In the structural formulae given herein and throughout the present specification, the following terms have the indicated meaning:

The term "halogen" means F, Cl, Br or I.

The term "$C_{1-6}$-alkyl" as used herein represents a saturated, branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, hexyl and the like.

The term "$C_{2-6}$-alkenyl" as used herein represents a branched or straight hydrocarbon group having from 3 to 8 carbon atoms and at least one double bond. Typical $C_{2-6}$-alkenyl groups include, but are not limited to, ethenyl, 1-propenyl, 2-propenyl, isopropenyl, 1,3-butadienyl, 1-butenyl, 2-butenyl, 1-pentenyl, 2-pentenyl, 1-hexenyl, 2-hexenyl, 1-ethylprop-2-enyl, 1,1-(dimethyl)prop-2-enyl, 1-ethylbut-3-enyl, 1,1-(dimethyl)but-2-enyl, and the like.

The term "$C_{2-6}$-alkynyl" as used herein represents a branched or straight hydrocarbon group having from 2 to 6 carbon atoms and at least one triple bond. Typical $C_{2-6}$-alkynyl groups include, but are not limited to, vinyl, 1-propynyl, 2-propynyl, isopropynyl, 1,3-buta-dynyl, 1-butynyl, 2-butynyl, 1-pentynyl, 2-pentynyl, 1-hexynyl, 2-hexynyl, 1-ethylprop-2-ynyl, 1,1-(dimethyl)prop-2-ynyl, 1-ethylbut-3-ynyl, 1,1-(dimethyl)but-2-ynyl, and the like.

The term "$C_{1-6}$-alkoxy" as used herein refers to the radical —O—$C_{1-6}$-alkyl, wherein $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "$C_{1-6}$-alkylthio as used herein refers to the radical —S—$C_{1-6}$-alkyl, wherein $C_{1-6}$-alkyl represents a saturated, branched or straight hydrocarbon groups having from 1 to 6 carbon atoms as defined above. Representative examples are methylthio, ethylthio, propylthio, butylthio, pentylthio, hexylthio, and the like The term "$C_{1-6}$-alkylsulfonyl" as used herein refers to the radical —$S(=O)_2$—$C_{1-6}$-alkyl, wherein $C_{1-6}$-alkyl represents a saturated, branched or straight hydrocarbon groups having from 1 to 6 carbon atoms as defined above. Representative examples are methylsulfonyl, ethylsulfonyl, propylsulfonyl, butylsulfonyl, pentylsulfonyl, hexylsulfonyl, and the like.

The term "$C_{1-6}$-alkylsulfinyl" as used herein refers to the radical —$S(=O)$—$C_{1-6}$-alkyl, wherein $C_{1-6}$-alkyl represents a saturated, branched or straight hydrocarbon groups having from 1 to 6 carbon atoms as defined above. Representative examples are methylsulfinyl, ethylsulfinyl, propylsulfinyl, butylsulfinyl, pentylsulfinyl, hexylsulfinyl, and the like.

The term "$C_{3-8}$-cycloalkyl" as used herein represents a monocyclic, carbocyclic group having from from 3 to 8 carbon atoms. Representative examples are cyclopropyl, cyclobutyl, cyclopentyl, cyclohexyl, cycloheptyl, cyclooctyl, and the like.

The term "$C_{3-8}$-cycloalkenyl" as used herein represents a monocyclic, carbocyclic, non-aromatic group having from 3 to 8 carbon atoms and at least one double bond. Representative examples are cyclopropenyl, cyclobutenyl, cyclopentenyl, cyclohexenyl, cycloheptenyl, cyclooctenyl and the like.

The term "aryl" as used herein is intended to include carbocyclic aromatic ring systems such as phenyl, biphenylyl, naphthyl, anthracenyl, phenanthrenyl, fluorenyl, indenyl, pentalenyl, azulenyl and the like. Aryl is also intended to include the partially hydrogenated derivatives of the carbocyclic systems enumerated above. Non-limiting examples of such partially hydrogenated derivatives are 1,2,3,4-tetrahydronaphthyl, 1,4-dihydronaphthyl and the like.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified.

When the groups in question are substituted with more than one substituent the substituents may be the same or different.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

DESCRIPTION OF THE INVENTION

In one embodiment of the invention n is 1.
In another embodiment n is 2.
In yet another embodiment $R^{1a}$ and $R^{1b}$ are hydrogen.
In still another embodiment $R^2$ is hydrogen.
In a further embodiment X is

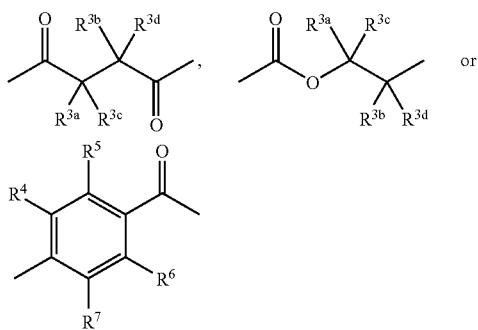

wherein $R^{3a}$, $R^{3b}$, $R^{3c}$, $R^{3d}$, $R^4$, $R^5$, $R^6$ and $R^7$ are as defined for formula (I).

In yet a further embodiment X is —C(=O)—CH$_2$—CH$_2$—C(=O)—, —C(=O)—O—CH$_2$—CH$_2$— or

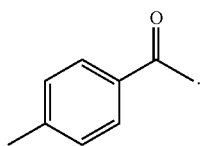

In still a further embodiment Z is

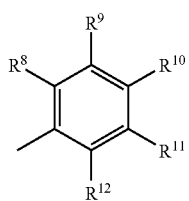

wherein $R^8$ to $R^{12}$ are as defined for formula (I).

In one embodiment thereof $R^8$ to $R^{12}$ independently are hydrogen, cyano, nitro, halogen, carboxy, guanidino, or amidino, $C_{1-6}$alkyl, $C_{1-6}$-alkoxy, $C_{2-6}$-alkenyl, $C_{2-6}$-alkynyl, $C_{1-6}$-alkylsulfonyl, $C_{1-6}$-alkylsulfinyl, $C_{1-6}$-alkylthio, $C_{1-6}$-alkylcarbonyl, $C_{3-8}$-cycloalkyl, $C_{3-8}$-cycloalkylcarbonyl, $C_{3-8}$-cycloalkenyl, aryl, arylsulfonyl, arylsulfinyl or arylthio, each of which may optionally be substituted with one or more groups selected from cyano, nitro, halogen, carboxy, guanidino, amidino, trifluoromethyl, trifluoromethoxy, —NR$^{13}$R$^{14}$, —NHC(=O)R$^{15}$ or —C(=O)NR$^{13}$R$^{14}$, and wherein aryl is selected from phenyl, biphenylyl, naphthyl, anthracenyl, phenanthrenyl, fluorenyl, indenyl, pentalenyl, azulenyl, 1,2,3,4-tetrahydronaphthyl, or 1,4-dihydronaphthyl, —NR$^{13}$R$^{14}$, —NHC(=O)R$^{15}$, —OC(=O)NR$^{13}$R$^{14}$, —NHC(=O)OR$^{16}$ or —C(=O)NR$^{13}$R$^{14}$, or $R^8$ and $R^9$, $R^9$ and $R^{10}$, $R^{10}$ and $R^{11}$, or $R^{11}$ and $R^{12}$ can be taken together to form a bridge selected from $C_{1-6}$-alkylene, —O—(CH$_2$)$_o$—O— and —O—(CH$_2$)$_o$—, In yet a further embodiment Z is

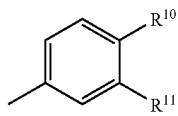

wherein $R^{10}$ to $R^{11}$ are as defined for formula (I).

In an embodiment thereof $R^{10}$ and $R^{11}$ are independently hydrogen, $C_{1-6}$-alkoxy, halogen or trifluoromethyl.

In another embodiment thereof at least one of $R^{10}$ and $R^{11}$ is different from hydrogen.

The compounds of the present invention may be chiral, and it is intended that any enantiomers, as separated, pure or partially purified enantiomers or racemic mixtures thereof are included within the scope of the invention.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates, which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds of the present invention interact with the histamine H3 receptor and are accordingly useful for the treatment of a wide variety of conditions and disorders in which histamine H3 receptor interactions are beneficial.

Accordingly, in another aspect the present invention relates to a compound of the general formula (I) as well as any diastereomer or enantiomer or tautomeric form thereof including mixtures of these or a pharmaceutically acceptable salt thereof for use as a pharmaceutical composition.

The invention also relates to pharmaceutical compositions comprising, as an active ingredient, at least one compound of the formula (I) or any diastereomer or enantiomer or tautomeric form thereof including mixtures of these or a pharmaceutically acceptable salt thereof together with one or more pharmaceutically acceptable carriers or diluents.

Furthermore, the invention relates to the use of a compound of the general formula (I) as well as any diastereomer or enantiomer or tautomeric form thereof including mixtures of these or a pharmaceutically acceptable salt thereof for the preparation of a pharmaceutical composition for the treatment of disorders and diseases related to the histamine H3 receptor.

In still another aspect, the invention relates to a method for the treatment of diseases and disorders related to the histamine H3 receptor the method comprising administering to a subject in need thereof an effective amount of a compound of the formula (I) or any diastereomer or enantiomer or tautomeric form thereof including mixtures of these or a pharmaceutically acceptable salt thereof or a pharmaceutical composition comprising the same.

In one aspect the invention relates to compounds with histamine H3 receptor antagonistic activity or inverse agonistic activity which may accordingly be useful in the treatment of a wide range of conditions and disorders in which histamine H3 receptor blockade is beneficial.

In another aspect the invention relates to compounds with histamine H3 receptor agonistic activity and which may accordingly be useful in the treatment of a wide range of conditions and disorders in which histamine H3 receptor activation is beneficial.

In a preferred embodiment of the invention the present compounds are used for the preparation of a pharmaceutical composition for the reduction of weight.

In a preferred embodiment of the invention the present compounds are used for the preparation of a pharmaceutical composition for the treatment of overweight or obesity.

In another preferred embodiment of the invention the present compounds are used for the preparation of a pharmaceutical composition for the suppression of appetite or satiety induction.

In a further preferred embodiment of the invention the present compounds are used for the preparation of a pharmaceutical composition for the prevention and/or treatment of disorders and diseases related to overweight or obesity such as atherosclerosis, hypertension, IGT (impaired glucose tolerance), diabetes, especially type 2 diabetes (NIDDM (non-insulin dependent diabetes mellitus)), dyslipidaemia, coronary heart disease, gallbladder disease, osteoarthritis and various types of cancer such as endometrial, breast, prostate and colon cancers.

In yet a further preferred embodiment of the invention the present compounds are used for the preparation of a pharmaceutical composition for the prevention and/or treatment of eating disorders such as bulimia and binge eating.

In a further preferred embodiment of the invention the present compounds are used for the preparation of a pharmaceutical composition for the treatment of IGT.

In a further preferred embodiment of the invention the present compounds are used for the preparation of a pharmaceutical composition for the treatment of type 2 diabetes. Such treatment includes inter alia treatment for the purpose of delaying or prevention of the progression from IGT to type 2 diabetes as well as delaying or prevention of the progression from non-insulin requiring type 2 diabetes to insulin requiring type 2 diabetes.

The compounds of the present invention may also be used for the treatment of airway disorders such as asthma, as anti-diarrhoeals and for the modulation of gastric acid secretion.

Furthermore, the compounds of the present invention may be used for the treatment of diseases associated with the regulation of sleep and wakefulness and for the treatment of narcolepsy and attention deficit disorder.

Moreover, the compounds of the invention may be used as CNS stimulants or as sedatives.

The present compounds may also be used for the treatment of conditions associated with epilepsy. Additionally, the present compounds may be used for the treatment of motion sickness and vertigo. Furthermore, they may be useful as regulators of hypothalamo-hypophyseal secretion, antidepressants, modulators of cerebral circulation, and in the treatment of irritable bowel syndrome.

Further, the compounds of the present invention may be used for the treatment of dementia and Alzheimer's disease.

The compounds of the present invention may also be useful for the treatment of allergic rhinitis, ulcer or anorexia.

The compounds of the present invention may furthermore be useful for the treatment of migraine, see McLeod et al., *The Journal of Pharmacology and Experimental Therapeutics* 287 (1998), 43–50, and for the treatment of myocardial infarction, see Mackins et al., *Expert Opinion on Investigational Drugs* 9 (2000), 2537–2542.

In a further aspect of the invention treatment of a patient with the present compounds is combined with diet and/or exercise.

In a further aspect of the invention the present compounds are administered in combination with one or more further active substances in any suitable ratio(s). Such further active agents may be selected from antiobesity agents, antidiabetics, antidyslipidemic agents, antihypertensive agents, agents for the treatment of complications resulting from or associated with diabetes and agents for the treatment of complications and disorders resulting from or associated with obesity.

Thus, in a further aspect of the invention the present compounds are administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, opioid antagonists (such as naltrexone), exendin-4, GLP-1 and ciliary neurotrophic factor.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

In still another embodiment the antiobesity agent is phendimetrazine, diethylpropion, fluoxetine, bupropion, topiramate or ecopipam.

In yet another embodiment the antiobesity agent is growth hormone, a growth factor such as prolactin or placental lactogen, or a growth hormone releasing compound.

In yet a further aspect the present compounds are administered in combination with one or more antidiabetic agents.

Relevant antidiabetic agents include insulin, insulin analogues and derivatives such as those disclosed in EP 0 792 290 (Novo Nordisk A/S), eg $N^{\epsilon B29}$-tetradecanoyl des (B30) human insulin, EP 0 214 826 and EP 0 705 275 (Novo Nordisk A/S), eg $Asp^{B28}$ human insulin, U.S. Pat. No. 5,504,188 (Eli Lilly), eg $Lys^{B28}$ $Pro^{B29}$ human insulin, EP 0 368 187 (Aventis), eg Lantus®, which are all incorporated herein by reference, GLP-1 derivatives such as those disclosed in WO 98/08871 (Novo Nordisk A/S), which is incorporated herein by reference, as well as orally active hypoglycaemic agents.

The orally active hypoglycaemic agents preferably comprise imidazolines, sulfonylureas, biguanides, meglitinides, oxadiazolidinediones, thiazolidinediones, insulin sensitizers, α-glucosidase inhibitors, agents acting on the ATP-dependent potassium channel of the β-cells eg potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In one embodiment of the invention the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention the present compounds are administered in combination with a sulfonylurea eg tolbutamide, chlorpropamide, tolazamide, glibenclamide, glipizide, glimepiride, gliclazide or glyburide.

In another embodiment of the invention the present compounds are administered in combination with a biguanide eg metformin.

In yet another embodiment of the invention the present compounds are administered in combination with a meglitinide eg repaglinide or nateglinide.

In still another embodiment of the invention the present compounds are administered in combination with a thiazolidinedione insulin sensitizer eg troglitazone, ciglitazone, pioglitazone, rosiglitazone, isaglitazone, darglitazone, englitazone, CS-011/Cl-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor eg voglibose, emiglitate, miglitol or acarbose.

In another embodiment of the invention the present compounds are administered in combination with an agent acting on the ATP-dependent potassium channel of the β-cells eg tolbutamide, glibenclamide, glipizide, gliclazide, BTS-67582 or repaglinide.

In yet another embodiment of the invention the present compounds may be administered in combination with nateglinide.

In still another embodiment, the present compounds are administered in combination with an antihyperlipidemic agent or antilipidemic agent, eg cholestyramine, colestipol, clofibrate, gemfibrozil, lovastatin, pravastatin, simvastatin, probucol or dextrothyroxine.

In still another embodiment of the invention the present compounds are administered in combination with an antilipidemic agent eg cholestyramine, colestipol, clofibrate, gemfibrozil, lovastatin, pravastatin, simvastatin, probucol or dextrothyroxine.

In another aspect of the invention, the present compounds are administered in combination with more than one of the above-mentioned compounds eg in combination with metformin and a sulfonylurea such as glyburide; a sulfonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with diet and/or exercise, one or more of the above-mentioned compounds and optionally one or more other active substances are considered to be within the scope of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the formula (I) contains a free base such salts are prepared in a conventional manner by treating a solution or suspension of a free base of the formula (I) with a chemical equivalent of a pharmaceutically acceptable acid, for example, inorganic and organic acids. Representative examples are mentioned above. Physiologically acceptable salts of a compound with a hydroxy group include the anion of said compound in combination with a suitable cation such as sodium or ammonium ion.

For parenteral administration, solutions of the novel compounds of the formula (I) in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet, which may be prepared by conventional tabletting techniques, may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition of the invention may comprise the compound of the formula (I) in combination with further pharmacologically active substances such as those described in the foregoing.

EXAMPLES

HPLC (Method A)

The reverse phase analysis was performed using UV detections at 214 and 254 nm on a 218TP54 4.6 mm×150 mm C-18 silica column, which was eluted at 1 ml/min at 42° C. The column was equilibrated with 5% acetonitrile, 85% water and 10% of a solution of 0.5% trifluoroacetic acid in water and eluted by a linear gradient from 5% acetonitrile, 85% water and 10% of a solution of 0.5% trifluoroacetic acid to 90% acetonitrile and 10% of a solution of 0.5% trifluoroacetic acid over 15 min.

HPLC (Method B)

The reverse phase analysis was performed using a Alliance Waters 2695 system fitted with a Waters 2487 dual band detector. UV detections were collected using a Symmetry C18, 3.5 μm, 3.0 mm×100 mm column. The column was eluted with a linear gradient of 5–90% acetonitrile, 90–0% water, and 5% trifluoroacetic acid (1.0%) in water over 8 min at a flow-rate of 1.0 min/min.

General Procedure (A)

A compound of formula (Iz) according to the invention may be prepared according to general procedure (A) as illustrated below:

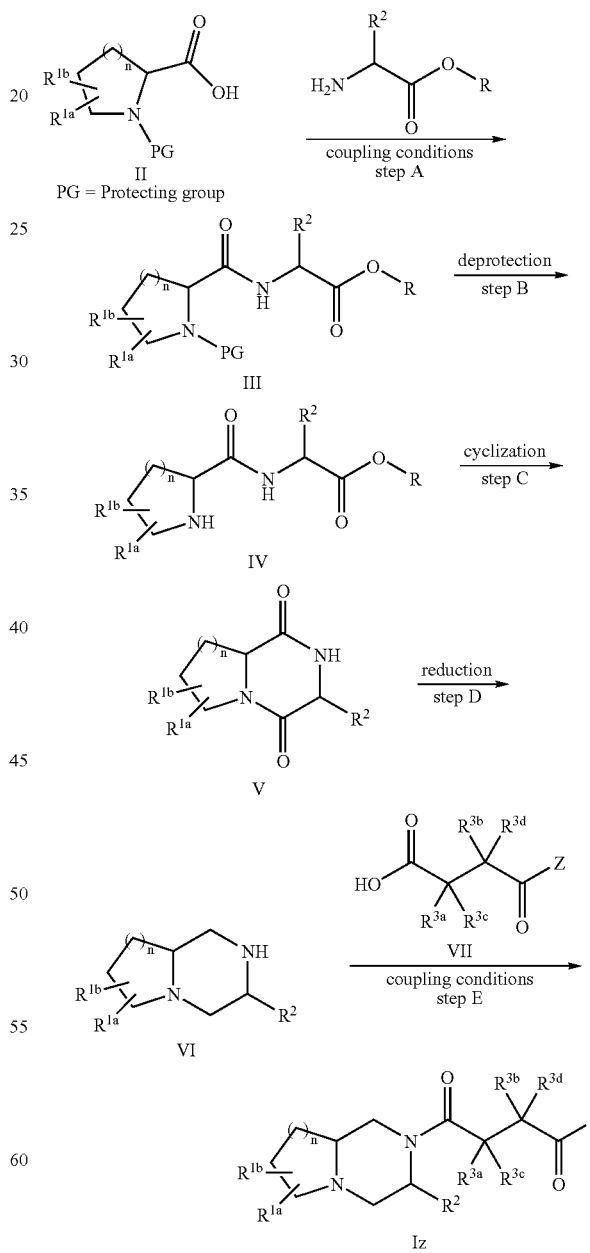

wherein $R^{1a}$, $R^{1b}$, $R^{3a}$, $R^{3b}$, $R^{3c}$, $R^{3d}$, $R^2$, n, and Z are as defined for formula (I)

Step A:

An amino acid of formula (II), which is protected at the amino group with a suitable protecting group (PG) known to a person skilled in the art and described in the literature (eg Protective Groups in Organic Synthesis, Greene, T. W., Wuts, P. G. M., $2^{nd}$ edition, John Wiley & Sons, New York) is reacted with an amino acid ester or a suitable salt thereof under amide-coupling conditions known to a person skilled in the art, eg in the presence of a suitable coupling reagent such as a suitable carbodiimide alone or a suitable carbodiimide in combination with a suitable helping agent such as 1-hydroxybenzotriazole, 1-hydroxy-7-azabenzotriazole, or 3-hydroxy-3H-dihydrobenzo[d][1,2,3]triazin-4-one, optionally in the presence of a base such as diisopropylethylamine or triethylamine to give an amide of formula (III), wherein R is the residue of an arbitrary alcohol or phenol.

Step B:

The protecting group of the amine is removed by a method known in the literature (eg Protective Groups in Organic Synthesis, Greene, T. W., Wuts, P. G. M., $2^{nd}$ edition, John Wiley & Sons, New York) to give the amine of formula (IV).

Step C:

The cyclization yielding a compound of formula (V) may be performed in the presence of a base such as eg triethylamine or diisopropylamine at a suitable temperature.

Step D:

A reduction with a suitable reduction agent, such as eg lithium aluminium hydride results in the formation of the bicyclic compound of formula (VI).

Step E:

A coupling with a suitable acid (VII) in the presence of a suitable coupling reagent known to a person skilled in the art such as eg a suitable carbodiimide alone or in combination with a suitable helping agent such as 1-hydroxybenzotriazole, 1-hydroxy-7-azabenzotriazole, or 3-hydroxy-3H-dihydrobenzo[d][1,2,3]triazin-4-one, optionally in the presence of a base such as diisopropylethylamine or triethylamine provides a compound of formula (Iz).

General Procedure (B)

A compound of formula (Iy) according to the invention may be prepared according to general procedure (B) as illustrated below:

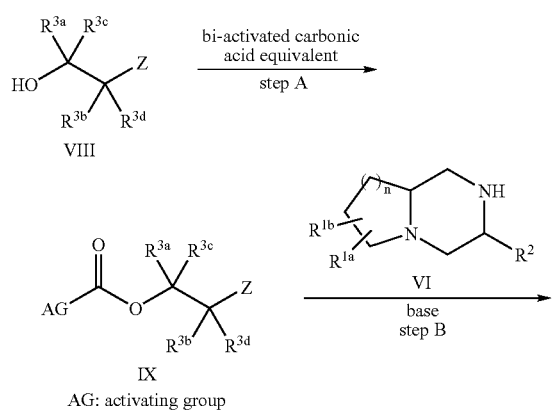

AG: activating group

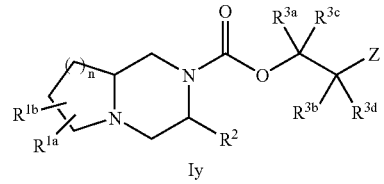

wherein $R^{1a}$, $R^{1b}$, $R^2$, $R^{3a}$, $R^{3b}$, $R^{3c}$, $R^{3d}$, n and Z are as defined for formula (I).

Step A:

An alcohol of the general formula (VIII) is reacted with a bi-activated carbonic acid equivalent known to a person skilled in the art eg 4-nitrophenyl chloroformate, carbonyl diimidazole or triphosgene, to give an activated carbon ester equivalent (IX).

Step B:

The compound of formula (IX) is reacted with the amine (VI) at a suitable temperature in the presence of a base such as diisopropylethylamine or triethylamine to yield a compound of formula (Iy).

General Procedure (C)

A compound of the general formula (Ix) may be prepared according to general procedure (C) illustrated below:

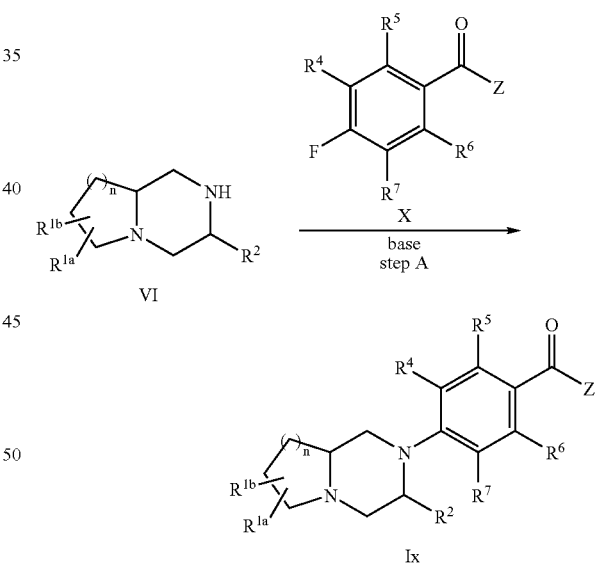

wherein $R^{1a}$, $R^{1b}$, $R^2$, $R^4$, $R^5$, $R^6$, $R^7$, n and Z are as defined for formula (I).

Step A:

The compound of formula (VI) is reacted with a fluoride of formula (X) in the presence of a suitable base such as triethylamine, diisopropylethylamine, or tert-buyltetra-mehylguanidine in a suitable solvent such as dimethylsulfoxide, N,N-dimethylformamide, N-methylpyrrolidinone, tetrahydrofuran or dichloromethane at a suitable temperature to provide the compound of formula (IX).

Example 1

General Procedure (A)

1-(3,4-Dimethoxyphenyl)-4-((S)-hexahydropyrrolo[1,2-a]pyrazin-2-yl)butane-1,4-dione

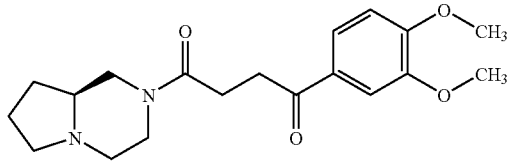

Step A: (S)-2-(((Methoxycarbonyl)methyl)carbamoyl)pyrrolidine-1-carboxylic acid tert-butyl ester

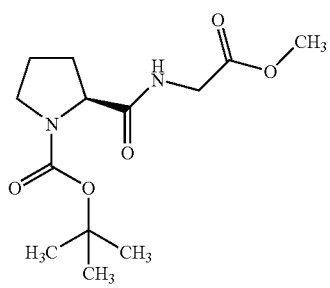

At 0° C., 1-(3-dimethylaminopropyl)-3-ethylcarbodiimide hydrochloride (8.82 g, 46 mmol) was added to a solution of 1-hydroxybenzotriazole (6.21 g, 46 mmol) and BOC-protected proline (10.0 g, 46 mmol) in a mixture of N,N-dimethylformamide (60 ml) and dichloromethane (60 ml). The reaction mixture was stirred for 30 min at 0° C. Glycine methyl ester hydrochloride (5.77 g, 46 mmol) and ethyldiisopropylamine (24 ml) were added successively. The reaction mixture was stirred for 16 hours, while it was warming up to room temperature. It was diluted with ethyl acetate (300 ml) and washed with a 10% aqueous solution of sodium hydrogen sulphate (300 ml). The aqueous phase was extracted with ethyl acetate (2×200 ml). The combined organic layers were washed with a saturated aqueous solution of sodium hydrogen carbonate (200 ml) and dried over magnesium sulphate. The solvent was removed in vacuo. The crude product was purified by flash chromatography on silica (200 g), using ethyl acetate as eluent, to give 10.25 g of (S)-2-(((methoxycarbonyl)methyl)carbamoyl)pyrrolidine-1-carboxylic acid tert-butyl ester.

$^1$H NMR (CDCl$_3$): δ 1.50 (s, 9H); 1.80–2.40 (m, 4H); 3.20–3.60 (m, 2H); 3.80 (s, 3H); 3.90–4.45 (m, 3H); 6.55 (br, 1H).

Step B: [((S)-Pyrrolidine-2-carbonyl)amino]acetic acid methyl ester trifluoroacetic acid salt

TFA

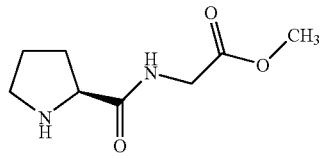

Trifluoroacetic acid (50 ml) was added to a solution of (S)-2-(((methoxycarbonyl)-methyl)carbamoyl)pyrrolidine-1-carboxylic acid tert-butyl ester (10.25 g, 36 mmol) in dichloromethane (50 ml). The reaction mixture was stirred for 1.25 hours. The solvent was removed in vacuo. The residue was dissolved in dichloromethane (50 ml). The solvent was removed in vacuo. The latter procedure was repeated once, to give 15.4 g of the crude trifluoroacetic acid salt of [((S)-pyrrolidine-2-carbonyl)amino]acetic acid methyl ester, which was used in the next step without purification.

$^1$H NMR (CDCl$_3$): δ2.05 (m, 3H); 2.50 (m, 1H); 3.50 (m, 2H); 3.75 (s, 3H); 4.05 (ABX, 2H); 4.75 (m, 1H); 7.80 (t, 1H); 10.60 (br, 2H).

Step C: (S)-Hexahydropyrrolo[1,2-a]pyrazine-1,4-dione

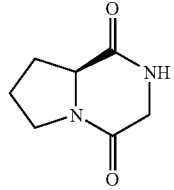

Triethylamine (75 ml, 540 mmol) was added to a solution of the crude trifluoroacetic acid salt of [((S)-pyrrolidine-2-carbonyl)amino]acetic acid methyl ester (15.4 g), which was isolated in the previous step, in methanol (300 ml). The reaction mixture was heated to reflux for 16 hours. It was cooled to room temperature. The solvent was removed in vacuo. The residue was suspended in 2-propanol (150 ml). The precipitation was isolated and dried in vacuo to give 4.38 g of (S)-hexahydropyrrolo[1,2-a]pyrazine-1,4-dione.

$^1$H NMR (DMSO-d$_6$): δ 1.85 (m, 3H); 2.15 (m, 1H); 3.35 (m, 2H); 3.55 (dd, 1H); 4.00 (d, 1H); 4.15 (m, 1H); 8.05 (br, 1H).

Step D: (S)-Octahydropyrrolo[1,2-a]pyrazine dihydrochloride salt

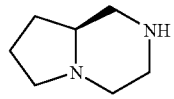

(S)-Hexahydropyrrolo[1,2-a]pyrazine-1,4-dione (3.08 g, 20 mmol) was added to a 1.0 M solution of lithium aluminium hydride in tetrahydrofuran (100 ml, 100 mmol). The mixture was heated to reflux for 1.5 hours. It was cooled to 0° C. Water (5 ml) was added carefully dropwise. A 1N solution of sodium hydroxide in water (5 ml) was added carfully dropwise. Water (10 ml) was added. The reaction mixture was left for 16 hours. The precipitation was removed by filtration through a plug of celite. A 2.8 M solution of hydrogen chloride in ethyl acetate (60 ml) was added to the filtrate. The solvent was removed in vacuo. The residue was dissolved in ethyl acetate. The solvent was removed in vacuo, to give 5.0 g of the crude dihydrochloride salt of (S)-octahydropyrrolo[1,2-a]pyrazine, which was used for the next step without further purification.

$^1$H NMR (DMSO-d$_6$): δ 1.70–2.35 (m, 4H); 3.00–4.15 (m, 9H).

Step E:

At 0° C., 1-(3-dimethylaminopropyl)-3-ethylcarbodiimide hydrochloride (479 mg, 2.5 mmol) was added to a solution of 3-(3,4-dimethoxybenzoyl)propionic acid (596 mg, 2.5 mmol) and 3-hydroxy-3H-dihydrobenzo[d][1,2,3]triazin-4-one (408 mg, 2.5 mmol) in a mixture of dichloromethane (10 ml) and N,N-dimethylformamide (10 ml). The reaction mixture was stirred for 25 min at 0° C. A solution of the crude dihydrochloride salt of (S)-octahydropyrrolo[1,2-a]pyrazine in N,N-dimethylformamide (4 ml) and ethyldiisopropylamine (3.0 ml, 17.5 mmol) were added successively. The reaction mixture was stirred for 16 hours, while it was warming up to room temperature. It was diluted with ethyl acetate (200 ml) and washed with a saturated aqueous solution of sodium hydrogen carbonate. The aqueous phase was extracted with ethyl acetate (2×100 ml). The combined organic layers were dried over magnesium sulphate. The solvent was removed in vacuo. The crude product was purified by HPLC on a C18-reversed phase column, using a mixture of 1% trifluoroacetic acid in water and acetonitrile as eluent, to give 148 mg of the title compound.

$^1$H NMR (CDCl$_3$, 2 sets of signals): δ 1.45 (m, 1H); 1.60–2.10 (m, 4H); 2.15 and 2.45 (both m, together 3H) 2.85 (m, 3H); 3.10 (m, 2H); 2.25 and 4.05 (m and d, together 3H); 3.91 (s, 3H); 3.93 (s, 3H); 4.60 and 4.75 (both d, together 1H); 6.90 (d, 1H); 7.60 (s, 1H); 7.70 (d, 1H); HPLC (method A): elution at 6.27 min; MS: Calc. for [M+H]$^+$: 347; Found: 347.

The title compound was transferred into its hydrochloride salt, by dissolving it in ethyl acetate (5 ml). A 2.8 M solution of hydrogen chloride in ethyl acetate (2 ml) was added. The solvent was removed in vacuo. The residue was dissolved in methanol (20 ml) and ethyl acetate (20 ml). The solvent was removed in vacuo.

$C_{19}H_{26}N_2O_4 \cdot HCl \cdot H_2O$ (346.43·3.46·18.02): Calc.: C 56.92H 7.29 N 6.99; Found: C 56.91H 6.89 N 6.77.

Example 2

General Procedure (A)

1-(4-Chlorophenyl)-4-((S)-hexahydropyrrolo[1,2-a]pyrazin-2-yl)butane-1,4-dione

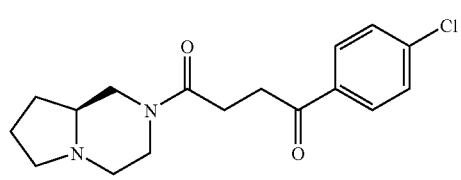

279 mg of the title compound were prepared as described for 1-(3,4-dimethoxy-phenyl)-4-((S)-hexahydropyrrolo[1,2-a]pyrazin-2-yl)butane-1,4-dione, using 3-(4-chlorobenzoyl) propionic acid instead of 3-(3,4-dimethoxybenzoyl) propionic acid.

$^1$H NMR (CDCl$_3$, 2 sets of signals): δ 1.45 (m, 1H); 1.70–2.05 and 2.15 (both m, together 6H); 2.40 and 2.70–3.00 (both m, together 3H); 3.00–3.20 and 3.20–3.40 (both m, together 5H); 3.93 and 4.05 (both d, together 1H); 4.60 and 4.70 (both d, together 1H); 7.40 (d, 2H); 7.95 (d, 2H); HPLC (method A): elution at 7.66 min; MS: Calc. for [M+H]$^+$: 321; Found: 321.

The title compound was transferred into its hydrochloride salt, by dissolving it in ethyl acetate (5 ml). A 2.8 M solution of hydrogen chloride in ethyl acetate (2 ml) was added. The solvent was removed in vacuo. The residue was dissolved in methanol (20 ml) and ethyl acetate (20 ml). The solvent was removed in vacuo.

Example 3

General Procedure (A)

1-(4-Chlorophenyl)-4-(octahydropyrido[1,2-a]pyrazin-2-yl)butane-1,4-dione

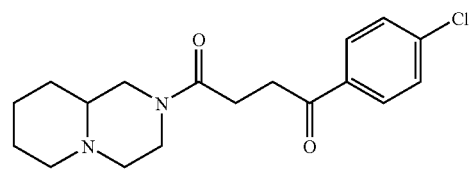

463 mg of the title compound were prepared as described for 1-(3,4-dimethoxyphenyl)-4-((S)-hexahydropyrrolo[1,2-a]pyrazin-2-yl)butane-1,4-dione, using 1-(tert-butoxycarbonyl)piperidine 2 carboxylic acid instead of BOC-protected proline and 3-(4-chlorobenzoyl)propanoic acid instead of 3-(3,4-dimethoxybenzoyl)propionic acid.

$^1$H NMR (CDCl$_3$, 2 sets of signals): δ 1.10–2.50 (m, 9H); 2.60–3.00 (m, 5H); 3.20–3.40 (m, 3H); 3.75 and 3.90 (both d, together 1H); 4.40 and 4.52 (both d, together 1H); 7.40 (d, 2H); 8.00 (d, 2H); HPLC (method A): elution at 7.79 min; MS: Calc. for [M+H]$^+$: 335; Found: 335.

The title compound was transferred into its hydrochloride salt, by dissolving it in ethyl acetate (5 ml). A 2.8 M solution of hydrogen chloride in ethyl acetate (2 ml) was added.

The solvent was removed in vacuo. The residue was dissolved in methanol (20 ml) and ethyl acetate (20 ml). The solvent was removed in vacuo.

$C_{18}H_{23}ClN_2O_2 \cdot HCl \cdot \frac{1}{2}H_2O$ (334.85·36.46·½ 18.02): Calc.: C 56.85H 6.63 N 7.37; Found: C 56.96H 6.57 N 7.35.

Example 4

General Procedure (A)

1-(3-Fluoro-4-methoxyphenyl)-4-(octahydropyrido[1,2-a]pyrazin-2-yl)butane-1,4-dione

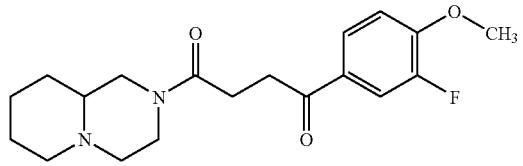

12 mg of the title compound were prepared as described for 1-(3,4-dimethoxyphenyl)-4-((S)-hexahydropyrrolo[1,2-a]pyrazin-2-yl)butane-1,4-dione, using 1-(tert-butoxycarbonyl)piperidine 2 carboxylic acid instead of BOC-protected proline and 3-(4-methoxy-3-fluorobenzoyl)propanoic acid instead of 3-(3,4-dimethoxybenzoyl)propionic acid.

$^1$H NMR (CDCl$_3$, 2 sets of signals): δ 1.25 (m, 2H); 1.55–2.50 (m, 8H); 2.85 (m, 5H); 3.30 (m, 2H); 3.75 and 3.90 (dt and d, together 1H); 3.98 (s, 3H); 4.40 and 4.55 (dt, and d, together 1H); 7.00 (t, 1H); 7.75 (d, 1H); 7.85 (d, 1H); HPLC (method A): elution at 7.23 min; MS: Calc. for [M+H]$^+$: 349; Found: 349.

The title compound was transferred into its hydrochloride salt, by dissolving it in ethyl acetate (5 ml). A 2.8 M solution of hydrogen chloride in ethyl acetate (2 ml) was added. The solvent was removed in vacuo. The residue was dissolved in methanol (20 ml) and ethyl acetate (20 ml). The solvent was removed in vacuo.

Example 5

General Procedure (A)

1-(3,4-Dimethoxyphenyl)-4-(octahydropyrido[1,2-a]pyrazin-2-yl)butane-1,4-dione

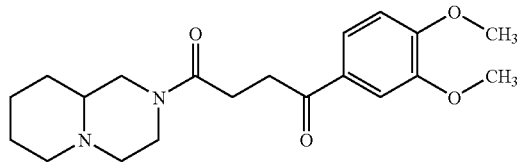

360 mg of the title compound were prepared as described for 1-(3,4-dimethoxyphenyl)-4-((S)-hexahydropyrrolo[1,2-a]pyrazin-2-yl)butane-1,4-dione, using 1-(tert-butoxycarbonyl)piperidine 2 carboxylic acid instead of BOC-protected proline.

$^1$H NMR (CDCl$_3$, 2 sets of signals): δ 1.10–1.95, 2.00–2.30, and 2.40 (m, m, and t, together 10H); 2.65–2.95 (m, 4H); 3.20–3.45 (m, 3H); 3.75 and 3.90 (d and m, together 1H); 3.95 (s, 3H); 3.97 (s, 3H); 4.40 and 4.45 (both d, together 1H); 6.90 (d, 1H); 7.55 (s, 1H); 7.70 (d, 1H); HPLC (method A): elution at 6.52 min; MS: Calc. for [M+H]$^+$: 361; Found: 361.

The title compound was transferred into its hydrochloride salt, by dissolving it in ethyl acetate (5 ml). A 2.8 M solution of hydrogen chloride in ethyl acetate (2 ml) was added. The solvent was removed in vacuo. The residue was dissolved in methanol (20 ml) and ethyl acetate (20 ml). The solvent was removed in vacuo.

C$_{20}$H$_{28}$N$_2$O$_4$.HCl (360.46·36.46): Cacl.: C 60.52H 7.36 N 7.06; Found: C 58.90H 7.12 N 6.82.

Example 6

General Procedure (A)

1-(3-Fluoro-4-methoxyphenyl)-4-((S)-octahydropyrido[1,2-a]pyrazin-2-yl)butane-1,4-dione

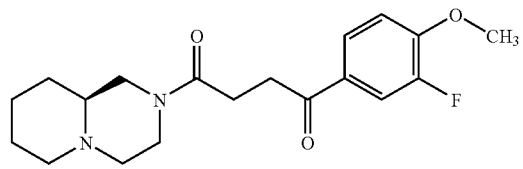

380 mg of the title compound were prepared as described for 1-(3,4-dimethoxyphenyl)-4-((S)-hexahydropyrrolo[1,2-a]pyrazin-2-yl)butane-1,4-dione, using (S)-1-(tert-butoxycarbonyl)piperidine 2 carboxylic acid instead of BOC-protected proline and 3-(3-fluoro-4-methoxybenzoyl)propionic acid instead of 3-(3,4-dimethoxybenzoyl)propionic acid.

$^1$H NMR (CDCl$_3$, 2 sets of signals): δ 1.25 (m, 2H); 1.50–2.45 (m, 8H); 2.85 (m, 5H); 3.20–3.45 (d, 2H); 3.75 and 3.90 (both m, together 1H); 3.95 (s, 3H); 4.40 and 4.55 (both m, together 1H); 7.00 (t, 1H); 7.75 (d, 1H); 7.85 (d, 1H); HPLC (method A): elution at 7.27 min; MS: Calc. for [M+H]$^+$: 349; Found: 349.

The title compound was transferred into its hydrochloride salt, by dissolving it in ethyl acetate (5 ml). A 2.8 M solution of hydrogen chloride in ethyl acetate (2 ml) was added. The solvent was removed in vacuo. The residue was dissolved in methanol (20 ml) and ethyl acetate (20 ml). The solvent was removed in vacuo.

C$_{19}$H$_{25}$N$_2$O$_3$.HCl.⅓H$_2$O (390.89): Cacl.: C 58.38H 6.88 N 7.17; Found: C 58.37H 6.92 N 7.04.

Example 7

General Procedure (A)

1-(3-Fluoro-4-methoxyphenyl)-4-((R)-octahydropyrido[1,2-a]pyrazin-2-yl)butane-1,4-dione

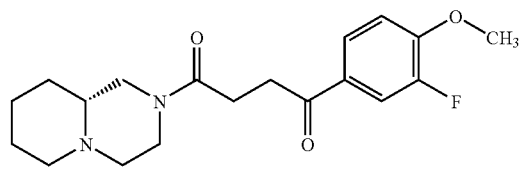

93 mg of the title compound were prepared as described for 1-(3,4-dimethoxyphenyl)-4-((S)-hexahydropyrrolo[1,2-a]pyrazin-2-yl)butane-1,4-dione, using (R)-1-(tert-butoxycarbonyl)piperidine 2 carboxylic acid instead of BOC-protected proline and 3-(3-fluoro-4-methoxybenzoyl)propionic acid instead of 3-(3,4-dimethoxybenzoyl)propionic acid.

$^1$H NMR (CDCl$_3$, 2 sets of signals): δ 1.25 (m, 2H); 1.50–2.45 (m, 8H); 2.85 (m, 5H); 3.20–3.45 (d, 2H); 3.75 and 3.90 (both m, together 1H); 3.95 (s, 3H); 4.40 and 4.55 (both m, together 1H); 7.00 (t, 1H); 7.75 (d, 1H); 7.85 (d, 1H); HPLC (method A): elution at 7.20 min; MS: Calc. for [M+H]$^+$: 349; Found: 349.

The title compound was transferred into its hydrochloride salt, by dissolving it in ethyl acetate (5 ml). A 2.8 M solution of hydrogen chloride in ethyl acetate (2 ml) was added. The solvent was removed in vacuo. The residue was dissolved in methanol (20 ml) and ethyl acetate (20 ml). The solvent was removed in vacuo.

C$_{19}$H$_{25}$N$_2$O$_3$.HCl.⅓H$_2$O (390.89): Cacl.: C 58.38 H 6.88 N 7.17; Found: C 58.37 H 6.92 N 7.04.

Example 8

General Procedure (B)

(S)-Octahydropyrido[1,2-a]pyrazine-2-carboxylic acid 2-(4-methoxyphenyl)ethyl ester

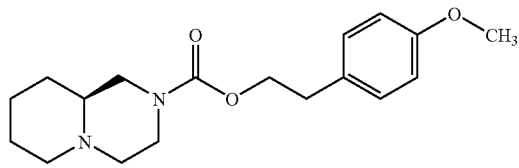

Preparation of (S)-Octahydropyrido[1,2-a]pyrazine (VI)

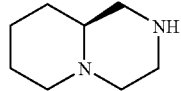

The dihydrochloride salt of (S)-octahydropyrido[1,2-a]pyrazine was prepared as described in steps A to D of example 1 using (S)-1-(tert-butoxycarbonyl)piperidine carboxylic acid instead of BOC-protected proline.

$^1$H NMR (DMSO-d$_6$): δ 1.1.40–2.00 (m, 6H); 2.90–3.60 (m, 9H); 10.20 (br, 2H); 12.15 (br, 1H).

Step A:

4-Nitrophenyl chloroformate (103 mg, 0.51 mmol) was added to a solution of 2-(4-methoxyphenyl)ethanol (78 mg, 0.51 mmol) and pyridine (0.082 ml, 1.02 mmol) in dichloromethane (15 ml). The reaction mixture was stirred at room temperature for 2.5 hours. It was diluted with dichloromethane (30 ml) and washed with water (3×30 ml). The organic layer was dried over magnesium sulphate.

Step B:

The solvent was removed in vacuo. The residue was dissolved in acetonitrile and added to a suspension of the dihydrochloride salt of (S)-octahydropyrido[1,2-a]pyrazine (138 mg, 0.64 mmol) and triethylamine (0.62 ml, 4.48 mmol) in dichloromethane (5 ml). The reaction mixture was stirred for 16 hours at room temperature. It was diluted with ethyl acetate (70 ml) and washed with a saturated aqueous solution of sodium hydrogencarbonate (50 ml). The aqueous solution was extracted with ethyl acetate (2×20 ml). The combined organic layers were dried over magnesium sulphate. The solvent was removed in vacuo. The crude product was purified by flash chromatography on silica (30 g), using dichloromethane/methanol/25% aqueous ammonia (100:10:1) as eluent. The resiude was dissolved in ethyl acetate (30 ml). It was extracted with a 10% aqueous solution of sodium hydrogen-sulphate (20 ml). The aqueous solution was made basic with a 1N sodium hydroxide solution and was extracted with ethyl acetate (2×20 ml). The combined extracts were dried over magnesium sulphate. The solvent was removed in vacuo to give 27 mg of the title compound.

$^1$H NMR (CDCl$_3$): δ 1.10–1.40 (m, 2H); 1.50–1.70 (m, 3H); 1.70–1.90 (m, 2H); 1.95–2.20 (m, 2H); 2.50–3.10 (m, 4H); 2.90 (t, 2H); 3.80 (s, 3H); 3.85–4.15 (m, 2H); 4.25 (t, 2H); 6.85 (d, 2H); 7.12 (d, 2H); HPLC (method A): elution at 7.80 min; MS: Calc. for [M+H]$^+$: 319; Found: 319.

The title compound was transferred into its hydrochloride salt, by dissolving it in ethyl acetate (5 ml). A 2.8 M solution of hydrogen chloride in ethyl acetate (2 ml) was added. The solvent was removed in vacuo. The residue was dissolved in methanol (20 ml) and ethyl acetate (20 ml). The solvent was removed in vacuo.

Example 9

General Procedure (B)

(R)-Octahydropyrido[1,2-a]pyrazine-2-carboxylic acid 2-(3-(trifluoromethyl)phenyl)ethyl ester

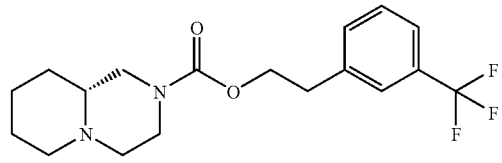

48 mg of the title compound was prepared as described for (S)-octahydropyrido[1,2-a]pyrazine-2-carboxylic acid 2-(4-methoxyphenyl)ethyl ester, using 2-(3-(trifluoromethyl)-phenyl)ethanol instead of 2-(4-methoxyphenyl)ethanol.

$^1$H NMR (CDCl$_3$, 2 sets of signals): δ 1.05–1.40 (m, 2H); 1.40–1.70 (m, 3H); 1.70–1.94 (m, 2H); 1.95–2.25 (m, 2H); 2.55 (m, 1H); 2.70 (m, 1H); 2.85 (m, 1H); 3.00 (m, 3H); 3.75, 3.95, and 4.05 (all m, together 2H); 4.30 (m, 2H); 7.45 (m, 2H); 7.50 (m, 2H); HPLC method A: elution at 9.09 min; MS: Calc. for [M+H]$^+$: 357; Found: 357.

The title compound was transferred into its hydrochloride salt, by dissolving it in ethyl acetate (5 ml). A 2.8 M solution of hydrogen chloride in ethyl acetate (2 ml) was added. The solvent was removed in vacuo. The residue was dissolved in methanol (20 ml) and ethyl acetate (20 ml). The solvent was removed in vacuo.

Example 10

General Procedure (C)

[3,5-Difluoro-4-((R)-octahydropyrido[1,2-a]pyrazin-2-yl)phenyl]-[phenyl]methanone

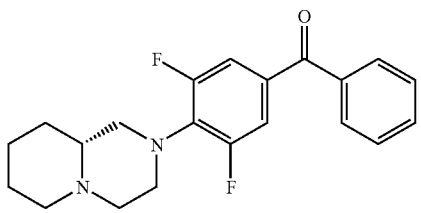

(R)-Octahydropyrido[1,2-a]pyrazine

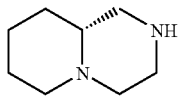

The dihydrochloride salt of (R)-octahydropyrido[1,2-a]pyrazine was synthesized analogously to the dihydrochloride salt of (S)-octahydropyrrolo[1,2-a]pyrazine, using (R)-1-(tert-butoxycarbonyl)piperidine 2 carboxylic acid instead of BOC-protected proline.

$^1$H NMR (DMSO-d$_6$): δ 1.35–1.95 (m, 6H); 2.85–3.60 (m, 9H); 10.25, 10.45, and 12.25 (all br, together 3H).

Step A:

A mixture of the dihydrochloride salt of (R)-octahydropyrido[1,2-a]pyrazine (300 mg, 1.41 mmol), triethylamine (1.17 ml, 8.46 mmol) and 3,4,5-trifluorobenzophenone (332 mg, 1.41. mmol; commercially available eg at Interchim, France) in dimethylsulfoxide (5 ml) was heated to 120° C. for 16 hours. The reaction mixture was cooled to room temperature and diluted with a solution of potassium carbonate (2.0 g) in water (50 ml). It was extracted with ethyl acetate (30 ml). The organic layer was dried over magnesium sulphate. The solvent was removed in vacuo. The crude product was purified by flash chromatography on silica (40 g), using first ethyl acetate/heptane (1:1,500 ml) and afterwards dichloromethane/methanol/—25% aqueous ammonia (100:10:1) as eluent, to give 132 mg of the title compound.

$^1$H NMR (CDCl$_3$, 2 sets of signals): δ 1.25 (m, 2H); 1.55 (d, 1H); 1.65 (m, 2H); 1.80 (d, 1H); 2.10 (m, 2H); 2.45 (td, 1H); 2.80 (d, 1H); 2.90 (d, 1H); 3.05 (t, 1H); 3.25 (d, 1H); 3.45 (m, 1H); 3.50 (t, 1H); 7.35 (m, 2H); 7.50 (m, 2H); 7.60 (t, 1H); 7.75 (d, 2H); HPLC method B: elution at 4.25 min; MS: calc. for [M+H]$^+$: 357; found: 357.

The title compound was transferred into its hydrochloride salt, by dissolving it in ethyl acetate (5 ml). A 2.8 M solution of hydrogen chloride in ethyl acetate (2 ml) was added. The solvent was removed in vacuo. The residue was dissolved in methanol (20 ml) and ethyl acetate (20 ml). The solvent was removed in vacuo.

Example 11

General Procedure (C)

(4-Fluorophenyl)-[4-((R)-octahydropyrido[1,2-a]pyrazin-2-yl)phenyl]methanone

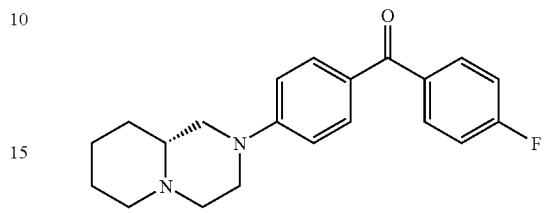

340 mg of the title compound were prepared as described for [3,5-difluoro-4-((R)-octahydropyrido[1,2-a]pyrazin-2-yl)phenyl]-[phenyl]methanone, using 4,4'-difluorobenzophenone instead of 3,4,5-trifluorobenzophenone.

$^1$H NMR (CDCl$_3$, 2 sets of signals): δ 1.35 (m, 2H); 1.65 (m, 3H); 1.80 (m, 1H); 2.05 (m, 2H); 2.35 (m, 1H); 2.65 (m, 1H); 3.40 (m, 2H); 3.10 (m, 1H); 3.65 (d, 1H); 3.80 (d, 1H); 6.90 (d, 2H); 7.15 (t, 2H); 7.75 (m, 4H); HPLC method A: elution at 8.46 min; MS: Calc. for [M+H]$^+$: 339; Found: 339.

The title compound was transferred into its hydrochloride salt, by dissolving it in ethyl acetate (5 ml). A 2.8 M solution of hydrogen chloride in ethyl acetate (2 ml) was added. The solvent was removed in vacuo. The residue was dissolved in methanol (20 ml) and ethyl acetate (20 ml). The solvent was removed in vacuo.

Example 12

General Procedure (C)

{[4-((R)-Octahydropyrido[1,2-a]pyrazin-2-yl)phenyl]}-{phenyl}methanone

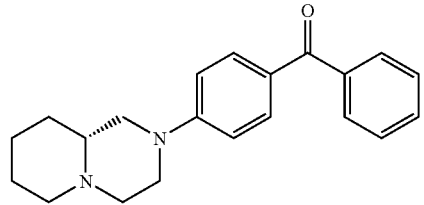

180 mg of the title compound were prepared as described for [3,5-difluoro-4-((R)-octahydropyrido[1,2-a]pyrazin-2-yl)phenyl]-[phenyl]methanone, using 4-fluorobenzophenone instead of 3,4,5-trifluorobenzophenone.

$^1$H NMR (CDCl$_3$, 2 sets of signals): δ 1.30 (m, 2H); 1.65 (m, 3H); 1.80 (m, 1H); 2.05 (m, 2H); 2.35 (dt, 2H); 2.65 (m, 1H); 2.90 (m, 2H); 3.10 (dt, 1H); 3.65 (d, 1H); 3.80 (d, 1H); 6.90 (d, 2H); 7.45 (m, 2H); 7.55 (m, 1H); 7.75 (m, 2H); 7.80 (d, 2H); HPLC method A: elution at 8.12 min; MS: Calc. for [M+H]$^+$: 321; Found: 321.

The title compound was transferred into its hydrochloride salt, by dissolving it in ethyl acetate (5 ml). A 2.8 M solution of hydrogen chloride in ethyl acetate (2 ml) was added. The solvent was removed in vacuo. The residue was dissolved in methanol (20 ml) and ethyl acetate (20 ml). The solvent was removed in vacuo.

Example 13

General Procedure (#)

(R)-2-[6-(4-Trifluoromethyl-phenyl)-pyridazin-3-yl]-octahydro-pyrido[1,2-a]pyrazine

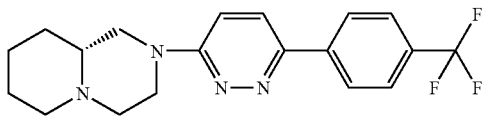

A mixture of the dihydrochloride salt of (R)-octahydro-pyrido[1,2-a]pyrazine (649 mg, 3.05 mmol), diisopropylethylamine (1.17 ml, 6.72 mmol), 3-chloro-6-(4-trifluoromethylphenyl)-pyridazine (290 mg, 1.12 mmol) and dimethylsulfoxide (1 ml) was heated in a closed vessel at 160° C. for 40 min. The reaction mixture was cooled to room temperature, diluted with dichloromethane (10 ml) and washed with water (2×15 ml) and brine (15 ml). The organic layer was dried over magnesium sulphate. The solvent was removed in vacuo to give 398 mg of the title compound as the free base.

$^1$H NMR (400 MHz, CDCl$_3$) δ 1.34 (broad t, 2H), 1.69 (m, 3H), 1.83 (m, 1H), 2.00–2.14 (m, 2H), 2.34 (dt, 1H), 2.81 (dd, 1H), 2.90 (broad d, 2H), 3.25 (dt, 1H), 4.32 (d, J=11.6 Hz, 2H), 6.99 (d, J=9.6 Hz, 1H), 7.67 (d, J=9.6 Hz, 1H), 7.72 (d, J=8.1 Hz, 2H), 8.12 (d, J=8.1 Hz, 2H).

HPLC-MS: m/z 362.8 (MH$^+$); Rt: 2.66 min.

Pharmacological Methods

The ability of the compounds to interact with the histamine H3 receptor can be determined by the following in vitro binding assays.

Binding assay I

The H3-receptor agonist ligand R-α-methyl[$^3$H]histamine (RAMHA) is incubated with isolated rat cortex cell-membranes at 25° C. for 1 hour, followed by a filtration of the incubate through Whatman GF/B filters. Radioactivity retained on the filters is measured using a beta counter.

Male Wistar rats (150–200 g) are decapitated and cerebral cortex is quickly dissected out and frozen immediately on dry ice. Tissue is kept at −80° C. until membrane preparation. During the membrane preparation the tissue is kept on ice all the time. Rat cerebral cortex is homogenized in 10 volumes (w/w) ice-cold Hepes buffer (20 mM Hepes, 5 mM MgCl$_2$ pH 7.1 (KOH)+1 mg/ml bacitracin) using an Ultra-Turrax homogenizer for 30 seconds. The homogenate is centrifuged at 140 g in 10 min. The supernatant is transferred to a new test tube and centrifuged for 30 min at 30 000 g. Pellet is resuspended in 5–10 ml Hepes buffer, homogenized and centrifuged for 10 min at 30 000 g. This short centrifugation step is repeated twice. After the last centrifugation the pellet is resuspended in 2–4 ml Hepes buffer and the protein concentration is determined. The membranes are diluted to a protein concentration of 5 mg/ml using Hepes buffer, aliquoted and stored at −80° C. until use.

50 µl test-compound, 100 µl membrane (200 µg/ml), 300 µl Hepes buffer and 50 µl R-α-methyl[$^3$H]histamine (1 nM) are mixed in a test tube. The compounds to be tested are dissolved in DMSO and further diluted in H$_2$O to the desired concentrations. Radioligand and membranes are diluted in Hepes buffer+1 mg/ml bacitracin. The mixture is incubated for 60 min at 25° C. Incubation is terminated by adding 5 ml ice-cold 0.9% NaCl, followed by rapid filtration through Whatman GF/B filters pre-treated for 1 hour with 0.5% polyethyleneimine. The filters are washed with 2×5 ml ice-cold NaCl. To each filter a 3 ml scintillation cocktail is added and the radioactivity retained is measured with a Packard Tri-Carb beta counter.

IC$_{50}$ values are calculated by non-linear regression analysis of binding curves (6 points minimum) using the windows program GraphPad Prism, GraphPad software, USA.

Binding Assay II

The human H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM (GIBCO-BRL) with glutamax, 10% foetal calf serum, 1% penicillin/streptavidin and 1 mg/ml G 418 at 37° C. and 5% CO$_2$. Before harvesting, the confluent cells are rinsed with PBS and incubated with Versene (proteinase, GIBCO-BRL) for approximately 5 min. The cells are flushed with PBS and DMEM and the cell suspension collected in a tube and centrifuged for 5–10 min at 420 g in a Heraeus Sepatech Megafuge 1.0. The pellet is resuspended in 10–20 vol. Hepes buffer (20 mM Hepes, 5 mM MgCl$_2$, pH 7.1 (KOH)) and homogenized for 10–20 seconds using an Ultra-Turrax homogenizer. The homogenate is centrifuged for 30 min at 30 000 g. The pellet is resuspended in 5–10 ml Hepes buffer, homogenized 5–10 seconds with the Ultra-Turrax and centrifuged for 10 min at 30 000 g. Following this centrifugation step, the membrane pellet is resuspended in 2–4 ml Hepes buffer, homogenized with a syringe or Teflon homogenizer, and the protein concentration determined. The membranes are diluted to a protein concentration of 1–5 mg/ml in Hepes buffer, aliquoted and kept at −80° C. until use.

Aliquots of the membrane suspension are incubated for 60 min at 25° C. with 30 pM [$^{125}$I]-iodoproxifan, a known compound with high affinity for the H3 receptor, and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analysed by nonlinear regression analysis.

When tested, the present compounds of the formula (I) generally show a high binding affinity to the histamine H3 receptor.

Functional Assay I

The ability of the compounds to interact with the histamine H3 receptor as agonists, inverse agonists and/or antagonists, is determined by an in vitro functional assay utilizing membranes from HEK 293 cell expressing the human H3 receptors.

The H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM with glutamax, 10% foetal calf serum, 1% penicillin/streptavidin and 1 mg/ml G418 at 37° C. and 5% CO$_2$.

The H3 receptor expressing cells are washed once with phosphate buffered saline (PBS) and harvested using versene (GIBCO-BRL). PBS is added and the cells are centrifuged for 5 min at 364 g. The cell pellet is resuspended in stimulation buffer to a concentration of 1×10⁶ cells/ml. cAMP accumulation is measured using the Flash Plate® cAMP assay (NEN™ Life Science Products). The assay is generally performed as described by the manufacturer. Briefly, 50 µl cell suspension is added to each well of the Flashplate which also contained 25 µl 40 µM isoprenaline, to stimulate cAMP generation, and 25 µl of test compound (either agonists or inverse agonists alone, or agonist and antagonist in combination). The assay can be run in "agonist-mode" which means that the test compound is added, in increasing concentration, on its own, to the cells, and cAMP is measured. If cAMP goes up, it is an inverse agonist; if CAMP does not change, it is a neutral antagonist, and if CAMP goes down, it is an agonist. The assay can also be run in the "antagonist-mode" which means that a test compound is added, in increasing concentrations, together with increasing concentrations of a known H3 agonist (eg RAMHA). If the compound is an antagonist, increasing concentrations of it cause a right-ward shift in the H3 agonist's dose-response curves. The final volume in each well is 100 µl. Test compounds are dissolved in DMSO and diluted in H$_2$O. The mixture is shaken for 5 min, and allowed to stand for 25 min at room temperature. The reaction is stopped with 100 µl "Detection Mix" per well. The plates are then sealed with plastic, shaken for 30 min, allowed to stand overnight, and finally the radioactivity is counted in the Cobra II auto gamma topcounter. EC$_{50}$ values are calculated by non-linear regression analysis of dose response curves (6 points minimum) using GraphPad Prism. Kb values are calculated by Schild plot analysis.

Functional Assay II

The ability of the compounds to bind and interact with the human, monkey or rat H3 receptor as agonists, inverse agonists and/or antagonists, is determined by a functional assay, named [$^{35}$S] GTPγS assay.

The human H3 receptor has the following sequence:

Met-Glu-Arg-Ala-Pro-Pro-Asp-Gly-Pro-Leu-Asn-Ala-

Ser-Gly-Ala-Leu-Ala-Gly-Glu-Ala-Ala-Ala-Ala-Gly-

Gly-Ala-Arg-Gly-Phe-Ser-Ala-Ala-Trp-Thr-Ala-Val-

Leu-Ala-Ala-Leu-Met-Ala-Leu-Leu-Ile-Val-Ala-Thr-

Val-Leu-Gly-Asn-Ala-Leu-Val-Met-Leu-Ala-Phe-Val-

Ala-Asp-Ser-Ser-Leu-Arg-Thr-Gln-Asn-Asn-Phe-Phe-

Leu-Leu-Asn-Leu-Ala-Ile-Ser-Asp-Phe-Leu-Val-Gly-

Ala-Phe-Cys-Ile-Pro-Leu-Tyr-Val-Pro-Tyr-Val-Leu-

Thr-Gly-Arg-Trp-Thr-Phe-Gly-Arg-Gly-Leu-Cys-Lys-

Leu-Trp-Leu-Val-Val-Asp-Tyr-Leu-Leu-Cys-Thr-Ser-

Ser-Ala-Phe-Asn-Ile-Val-Leu-Ile-Ser-Tyr-Asp-Arg-

Phe-Leu-Ser-Val-Thr-Arg-Ala-Val-Ser-Tyr-Arg-Ala-

Gln-Gln-Gly-Asp-Thr-Arg-Arg-Ala-Val-Arg-Lys-Met-

Leu-Leu-Val-Trp-Val-Leu-Ala-Phe-Leu-Leu-Tyr-Gly-

Pro-Ala-Ile-Leu-Ser-Trp-Glu-Tyr-Leu-Ser-Gly-Gly-

Ser-Ser-Ile-Pro-Glu-Gly-His-Cys-Tyr-Ala-Glu-Phe-

Phe-Tyr-Asn-Trp-Tyr-Phe-Leu-Ile-Thr-Ala-Ser-Thr-

-continued

Leu-Glu-Phe-Phe-Thr-Pro-Phe-Leu-Ser-Val-Thr-Phe-

Phe-Asn-Leu-Ser-Ile-Tyr-Leu-Asn-Ile-Gln-Arg-Arg-

Thr-Arg-Leu-Arg-Leu-Asp-Gly-Ala-Arg-Glu-Ala-Ala-

Gly-Pro-Glu-Pro-Pro-Pro-Glu-Ala-Gln-Pro-Ser-Pro-

Pro-Pro-Pro-Pro-Gly-Cys-Trp-Gly-Cys-Trp-Gln-Lys-

Gly-His-Gly-Glu-Ala-Met-Pro-Leu-His-Arg-Tyr-Gly-

Val-Gly-Glu-Ala-Ala-Val-Gly-Ala-Glu-Ala-Gly-Glu-

Ala-Thr-Leu-Gly-Gly-Gly-Gly-Gly-Gly-Ser-Val-

Ala-Ser-Pro-Thr-Ser-Ser-Ser-Gly-Ser-Ser-Ser-Arg-

Gly-Thr-Glu-Arg-Pro-Arg-Ser-Leu-Lys-Arg-Gly-Ser-

Lys-Pro-Ser-Ala-Ser-Ser-Ala-Ser-Leu-Glu-Lys-Arg-

Met-Lys-Met-Val-Ser-Gln-Ser-Phe-Thr-Gln-Arg-Phe-

Arg-Leu-Ser-Arg-Asp-Arg-Lys-Val-Ala-Lys-Ser-Leu-

Ala-Val-Ile-Val-Ser-Ile-Phe-Gly-Leu-Cys-Trp-Ala-

Pro-Tyr-Thr-Leu-Leu-Met-Ile-Ile-Arg-Ala-Ala-Cys-

His-Gly-His-Cys-Val-Pro-Asp-Tyr-Trp-Tyr-Glu-Thr-

Ser-Phe-Trp-Leu-Leu-Trp-Ala-Asn-Ser-Ala-Val-Asn-

Pro-Val-Leu-Tyr-Pro-Leu-Cys-His-His-Ser-Phe-Arg-

Arg-Ala-Phe-Thr-Lys-Leu-Leu-Cys-Pro-Gln-Lys-Leu-

Lys-Ile-Gln-Pro-His-Ser-Ser-Leu-Glu-His-Cys-Trp-

Lys

The monkey H3 receptor has the following sequence:

Met-Glu-Arg-Ala-Pro-Pro-Asp-Gly-Pro-Leu-Asn-Ala-

Ser-Gly-Ala-Leu-Ala-Gly-Glu-Ala-Ala-Ala-Ala-Gly-

Gly-Ala-Arg-Gly-Phe-Ser-Ala-Ala-Trp-Thr-Ala-Val-

Leu-Ala-Ala-Leu-Met-Ala-Leu-Leu-Ile-Val-Ala-Thr-

Val-Leu-Gly-Asn-Ala-Leu-Val-Met-Leu-Ala-Phe-Val-

Ala-Asp-Ser-Ser-Leu-Arg-Thr-Gln-Asn-Asn-Phe-Phe-

Leu-Leu-Asn-Leu-Ala-Ile-Ser-Asp-Phe-Leu-Val-Gly-

Ala-Phe-Cys-Ile-Pro-Leu-Tyr-Val-Pro-Tyr-Val-Leu-

Thr-Gly-Arg-Trp-Thr-Phe-Gly-Arg-Gly-Leu-Cys-Lys-

Leu-Trp-Leu-Val-Val-Asp-Tyr-Leu-Leu-Cys-Thr-Ser-

Ser-Ala-Phe-Asn-Ile-Val-Leu-Ile-Ser-Tyr-Asp-Arg-

Phe-Leu-Ser-Val-Thr-Arg-Ala-Val-Ser-Tyr-Arg-Ala-

Gln-Gln-Gly-Asn-Thr-Arg-Arg-Ala-Val-Arg-Lys-Met-

Leu-Leu-Val-Trp-Val-Leu-Ala-Phe-Leu-Leu-Tyr-Gly-

Pro-Ala-Ile-Leu-Ser-Trp-Glu-Tyr-Leu-Ser-Gly-Gly-

Ser-Ser-Ile-Pro-Glu-Gly-His-Cys-Tyr-Ala-Glu-Phe-

Phe-Tyr-Asn-Trp-Tyr-Phe-Leu-Ile-Thr-Ala-Ser-Thr-

-continued
Leu-Glu-Phe-Phe-Thr-Pro-Phe-Leu-Ser-Val-Thr-Phe-

Phe-Asn-Leu-Ser-Ile-Tyr-Leu-Asn-Ile-Gln-Arg-Arg-

Thr-Arg-Leu-Arg-Leu-Asp-Gly-Ala-Arg-Glu-Ala-Gly-

Gly-Pro-Glu-Pro-Pro-Glu-Ala-Gln-Pro-Ser-Pro-

Pro-Pro-Pro-Pro-Gly-Cys-Trp-Gly-Cys-Trp-Gln-Lys-

Gly-His-Gly-Glu-Ala-Met-Pro-Leu-His-Arg-Tyr-Gly-

Val-Gly-Glu-Ala-Ala-Ala-Gly-Ala-Glu-Ala-Gly-Glu-

Thr-Ala-Leu-Gly-Gly-Gly-Gly-Gly-Gly-Ser-Ala-

Ala-Ser-Pro-Thr-Ser-Ser-Ser-Gly-Ser-Ser-Ser-Arg-

Gly-Thr-Glu-Arg-Pro-Arg-Ser-Leu-Lys-Arg-Gly-Ser-

Lys-Pro-Ser-Ala-Ser-Ser-Ala-Ser-Leu-Glu-Lys-Arg-

Met-Lys-Met-Val-Ser-Gln-Ser-Phe-Thr-Gln-Arg-Phe-

Arg-Leu-Ser-Arg-Asp-Arg-Lys-Val-Ala-Lys-Ser-Leu-

Ala-Val-Ile-Val-Ser-Ile-Phe-Gly-Leu-Cys-Trp-Ala-

Pro-Tyr-Thr-Leu-Leu-Met-Ile-Ile-Arg-Ala-Ala-Cys-

His-Gly-His-Cys-Val-Pro-Asp-Tyr-Trp-Tyr-Glu-Thr-

Ser-Phe-Trp-Leu-Leu-Trp-Ala-Asn-Ser-Ala-Val-Asn-

Pro-Val-Leu-Tyr-Pro-Leu-Cys-His-His-Ser-Phe-Arg-

Arg-Ala-Phe-Thr-Lys-Leu-Leu-Cys-Pro-Gln-Lys-Leu-

Lys-Ile-Gln-Pro-His-Ser-Ser-Leu-Glu-Gln-Cys-Trp-

Lys

The rat H3 receptor has the following sequence:

Met-Glu-Arg-Ala-Pro-Pro-Asp-Gly-Leu-Met-Asn-Ala-

Ser-Gly-Thr-Leu-Ala-Gly-Glu-Ala-Ala-Ala-Ala-Gly-

Gly-Ala-Arg-Gly-Phe-Ser-Ala-Ala-Trp-Thr-Ala-Val-

Leu-Ala-Ala-Leu-Met-Ala-Leu-Leu-Ile-Val-Ala-Thr-

Val-Leu-Gly-Asn-Ala-Leu-Val-Met-Leu-Ala-Phe-Val-

Ala-Asp-Ser-Ser-Leu-Arg-Thr-Gln-Asn-Asn-Phe-Phe-

Leu-Leu-Asn-Leu-Ala-Ile-Ser-Asp-Phe-Leu-Val-Gly-

Ala-Phe-Cys-Ile-Pro-Leu-Tyr-Val-Pro-Tyr-Val-Leu-

Thr-Gly-Arg-Trp-Thr-Phe-Gly-Arg-Gly-Leu-Cys-Lys-

Leu-Trp-Leu-Val-Val-Asp-Tyr-Leu-Leu-Cys-Ala-Ser-

Ser-Val-Phe-Asn-Ile-Val-Leu-Ile-Ser-Tyr-Asp-Arg-

Phe-Leu-Ser-Val-Thr-Arg-Ala-Val-Ser-Tyr-Arg-Ala-

Gln-Gln-Gly-Asp-Thr-Arg-Arg-Ala-Val-Arg-Lys-Met-

Ala-Leu-Val-Trp-Val-Leu-Ala-Phe-Leu-Leu-Tyr-Gly-

Pro-Ala-Ile-Leu-Ser-Trp-Glu-Tyr-Leu-Ser-Gly-Gly-

Ser-Ser-Ile-Pro-Glu-Gly-His-Cys-Tyr-Ala-Glu-Phe-

Phe-Tyr-Asn-Trp-Tyr-Phe-Leu-Ile-Thr-Ala-Ser-Thr-

-continued
Leu-Glu-Phe-Phe-Thr-Pro-Phe-Leu-Ser-Val-Thr-Phe-

Phe-Asn-Leu-Ser-Ile-Tyr-Leu-Asn-Ile-Gln-Arg-Arg-

Thr-Arg-Leu-Arg-Leu-Asp-Gly-Gly-Arg-Glu-Ala-Gly-

Pro-Glu-Pro-Pro-Pro-Asp-Ala-Gln-Pro-Ser-Pro-Pro-

Pro-Ala-Pro-Pro-Ser-Cys-Trp-Gly-Cys-Trp-Pro-Lys-

Gly-His-Gly-Glu-Ala-Met-Pro-Leu-His-Arg-Tyr-Gly-

Val-Gly-Glu-Ala-Gly-Pro-Gly-Val-Glu-Ala-Gly-Glu-

Ala-Ala-Leu-Gly-Gly-Gly-Ser-Gly-Gly-Gly-Ala-Ala-

Ala-Ser-Pro-Thr-Ser-Ser-Ser-Gly-Ser-Ser-Ser-Arg-

Gly-Thr-Glu-Arg-Pro-Arg-Ser-Leu-Lys-Arg-Gly-Ser-

Lys-Pro-Ser-Ala-Ser-Ser-Ala-Ser-Leu-Glu-Lys-Arg-

Met-Lys-Met-Val-Ser-Gln-Ser-Ile-Thr-Gln-Arg-Phe-

Arg-Leu-Ser-Arg-Asp-Lys-Lys-Val-Ala-Lys-Ser-Leu-

Ala-Ile-Ile-Val-Ser-Ile-Phe-Gly-Leu-Cys-Trp-Ala-

Pro-Tyr-Thr-Leu-Leu-Met-Ile-Ile-Arg-Ala-Ala-Cys-

His-Gly-Arg-Cys-Ile-Pro-Asp-Tyr-Trp-Tyr-Glu-Thr-

Ser-Phe-Trp-Leu-Leu-Trp-Ala-Asn-Ser-Ala-Val-Asn-

Pro-Val-Leu-Tyr-Pro-Leu-Cys-His-Tyr-Ser-Phe-Arg-

Arg-Ala-Phe-Thr-Lys-Leu-Leu-Cys-Pro-Gln-Lys-Leu-

Lys-Val-Gln-Pro-His-Gly-Ser-Leu-Glu-Gln-Cys-Trp-

Lys

The assay measures the activation of G proteins by catalyzing the exchange of guanosine 5'-diphosphate (GDP) by guanosine 5'-triphosphate (GTP) at the α-subunit. The GTP-bounded G proteins dissociate into two subunits, $G\alpha_{GTP}$ and Gαγ, which in turn regulate intracellular enzymes and ion channels. GTP is rapidly hydrolysed by the Gα-subunit (GTPases) and the G protein is deactivated and ready for a new GTP exchange cycle. To study the function of ligand induced G protein coupled receptor (GPCR) activation by an increase in guanine nucleotide exchange at the G proteins, the binding of [$^{35}$S]-guanosine-5'-O-(3-thio) triphosphate ([$^{35}$S] GTPγS), a non-hydrolysed analogue of GTP, is determined. This process can be monitored in vitro by incubating cell membranes containing the G protein coupled receptor H3 with GDP and [$^{35}$S] GTPγS. Cell membranes are obtained from CHO cells stably expressing the human H3 receptor or from HEK 293 cells stably expressing the rat or monkey H3 receptor. The cells are washed twice in PBS, harvested with PBS+1 mM EDTA, pH 7.4 and centrifuged at 280 g for 5 min. The cell pellet is homogenized in 10 ml ice-cold Hepes buffer (20 mM Hepes, 10 mM EDTA pH 7.4 (NaOH)) using an Ultra-Turrax homogenizer for 30 seconds and centrifuged for 15 min at 30.000 g. Following this centrifugation step, the membrane pellet is resuspended in 10 ml ice-cold Hepes buffer (20 mM Hepes, 0.1 mM EDTA pH 7.4 (NaOH)) and homogenized as describe above. This procedure is repeated twice except for the last homogenization step, the protein concentration is determined and membranes are diluted to a protein concentration of 2 mg/ml, aliquoted and kept at −80° C. until use.

In order to study the presence and the potency of an inverse agonist/antagonist the H3-receptor agonist ligand R-α-methyl histamine (RAMHA) is added. The ability of the test compound to counteract the effect of RAMHA is measured. When studying the effect of an agonist RAMHA is not added to the assay medium. The test compound is diluted in the assay buffer (20 mM HEPES, 120 mM NaCl, 10 mM $MgCl_2$ pH 7.4 (NaOH)) at various concentrations followed by addition of $10^{-8}$ nM RAMHA (only in the case where an inverse agonist/antagonist is examined), 3 µM GDP, 2.5 µg membranes, 0.5 mg SPA beads and 0.1 nM [$^{35}$S] GTPγS and incubated for 2 hours by slightly shaking at room temperature. For the rat and monkey H3 receptor 10 µg membranes including 10 µg/ml saponin are used. The plates are centrifuged at 420 g for 10 min and the radioactivity is measured using a Top-counter. The results are analyzed by non linear regression and the $IC_{50}$ value is determined.

RAMHA and other H3 agonists stimulate the binding of [$^{35}$S] GTPγS to membranes expressing the H3 receptor. In the antagonist/inverse agonist test, the ability of increasing amounts of test compound to inhibit the increased [$^{35}$S] GTPγS binding by $10^{-8}$ M RAMHA is measured as a decrease in radioactivity signal. The $IC_{50}$ value determined for an antagonist is the ability of this compound to inhibit the effect of $10^{-8}$ M RAMHA by 50%. In the agonist test, the ability of increasing amounts of test compound is measured as an increase in radioactivity signal. The $EC_{50}$ value determined for an agonist, is the ability of this compound to increase the signal by 50% of the maximal signal that is obtained by $10^5$ M RAMHA.

Preferably, the antagonists and agonists according to the invention have an $IC_{50}/EC_{50}$ value as determined by one or more of the assays of less than 10 µM, more preferred of less than 1 µM, and even more preferred of less than 500 nM, such as of less than 100 nM.

The Open Cage Schedule-fed Rat Model

The ability of the present compounds to reduce weight is determined using the in vivo open cage Schedule-fed rat model.

Sprague-Dawley (SD) male rats of an age of about 1½ to 2 months and a weight of about 200–250 g are purchased from Møllegård Breeding and Research Centre A/S (Denmark). On arrival they are allowed some days of acclimatisation before being placed in individual open plastic cages. They are habituated to the presence of food (Altromin pelleted rat chow) in their home cage only during 7 hours in the morning from 07.30 to 14.30 all days a week. Water is present ad libitum. As the consumption of food has stabilised after 7 to 9 days, the animals are ready for use.

Each animal is used only once to avoid carry-over effects between treatments. During the test sessions, the test compound is administered intraperitoneally or orally 30 min before the start of the sessions. One group of animals is administered the test compound at different doses and a control group of animals is given a vehicle. Food and water intake are monitored at 1, 2 and 3 hours post administration.

Any side effects may rapidly be discovered (barrel-rolling, bushy fur etc.) since the animals are kept in transparent plastic cages to enable continuous monitoring.

What is claimed is:

1. A compound selected from the following group:
   1-(3,4-Dimethoxyphenyl)-4-((S)-hexahydropyrrolo[1,2-a]pyrazin-2-yl)butane-1,4-dione,
   1-(4-Chlorophenyl)-4-((S)-hexahydropyrrolo[1,2-a]pyrazin-2-yl)butane-1,4-dione,
   1-(4-Chlorophenyl)-4-(octahydropyrido[1,2-a]pyrazin-2-yl)butane-1,4-dione,
   1-(3-Fluoro-4-methoxyphenyl)-4-(octahydropyrido[1,2-a]pyrazin-2-yl)butane-1,4-dione,
   1-(3,4-Dimethoxyphenyl)-4-(octahydropyrido[1,2-a]pyrazin-2-yl)butane-1,4-dione,
   1-(3-Fluoro-4-methoxyphenyl)-4-((S)-octahydropyrido[1,2-a]pyrazin-2-yl)butane-1,4-dione,
   1-(3-Fluoro-4-methoxyphenyl)-4-((R)-octahydropyrido[1,2-a]pyrazin-2-yl)butane-1,4-dione;
   (S)-Octahydropyrido[1,2-a]pyrazine-2-carboxylic acid 2-(4-methoxyphenyl)ethyl ester,
   (R)-Octahydropyrido[1,2-a]pyrazine-2-carboxylic acid 2-(3-(trifluoromethyl)phenyl)ethyl ester,
   [3,5-Difluoro-4-((R)-octahydropyrido[1,2-a]pyrazin-2-yl)phenyl]-[phenyl]methanone,
   (4-Fluorophenyl)-[4-((R)-octahydropyrido[1,2-a]pyrazin-2-yl)phenyl]methanone,
   {[4-((R)-Octahydropyrido[1,2-a]pyrazin-2-yl)phenyl]}-{phenyl}methanone, and
   (R)-2-[6-(4-Trifluoromethyl-phenyl)-pyridazin-3-yl]-octahydro-pyrido[1,2-a]pyrazine,
   as well as any diastereomer or enantiomer or tautomeric form thereof or mixtures of these or a pharmaceutically acceptable salt thereof.

2. A pharmaceutical composition comprising, as an active ingredient, at least one compound according to claim 1 together with one or more pharmaceutically acceptable carriers or excipients.

3. A pharmaceutical composition according to claim 2 in unit dosage form, comprising from about 0.05 mg to about 1000 mg of the compound.

4. A pharmaceudcal composition according to claim 2 in unit dosage form,
   comprising from about 0.1 mg to about 500 mg of the compound.

5. A pharmaceutical composition according to claim 2 in unit dosage form,
   comprising from about 0.5 mg to about 200 mg of the compound.

* * * * *

SEQUENCE LISTING

<160> NUMBER OF SEQ ID NOS: 3

<210> SEQ ID NO 1
<211> LENGTH: 445
<212> TYPE: PRT
<213> ORGANISM: Homo Sapiens

<400> SEQUENCE: 1

```
Met Glu Arg Ala Pro Pro Asp Gly Pro Leu Asn Ala Ser Gly Ala Leu
1               5                   10                  15

Ala Gly Glu Ala Ala Ala Ala Gly Gly Ala Arg Gly Phe Ser Ala Ala
            20                  25                  30

Trp Thr Ala Val Leu Ala Ala Leu Met Ala Leu Leu Ile Val Ala Thr
        35                  40                  45

Val Leu Gly Asn Ala Leu Val Met Leu Ala Phe Val Ala Asp Ser Ser
    50                  55                  60

Leu Arg Thr Gln Asn Asn Phe Phe Leu Leu Asn Leu Ala Ile Ser Asp
65                  70                  75                  80

Phe Leu Val Gly Ala Phe Cys Ile Pro Leu Tyr Val Pro Tyr Val Leu
                85                  90                  95

Thr Gly Arg Trp Thr Phe Gly Arg Gly Leu Cys Lys Leu Trp Leu Val
            100                 105                 110

Val Asp Tyr Leu Leu Cys Thr Ser Ser Ala Phe Asn Ile Val Leu Ile
        115                 120                 125

Ser Tyr Asp Arg Phe Leu Ser Val Thr Arg Ala Val Ser Tyr Arg Ala
    130                 135                 140
```

-continued

```
Gln Gln Gly Asp Thr Arg Arg Ala Val Arg Lys Met Leu Leu Val Trp
145                 150                 155                 160

Val Leu Ala Phe Leu Leu Tyr Gly Pro Ala Ile Leu Ser Trp Glu Tyr
            165                 170                 175

Leu Ser Gly Gly Ser Ser Ile Pro Glu Gly His Cys Tyr Ala Glu Phe
        180                 185                 190

Phe Tyr Asn Trp Tyr Phe Leu Ile Thr Ala Ser Thr Leu Glu Phe Phe
    195                 200                 205

Thr Pro Phe Leu Ser Val Thr Phe Phe Asn Leu Ser Ile Tyr Leu Asn
210                 215                 220

Ile Gln Arg Arg Thr Arg Leu Arg Leu Asp Gly Ala Arg Glu Ala Ala
225                 230                 235                 240

Gly Pro Glu Pro Pro Glu Ala Gln Pro Ser Pro Pro Pro Pro
                245                 250                 255

Gly Cys Trp Gly Cys Trp Gln Lys Gly His Gly Glu Ala Met Pro Leu
            260                 265                 270

His Arg Tyr Gly Val Gly Glu Ala Ala Val Gly Ala Glu Ala Gly Glu
        275                 280                 285

Ala Thr Leu Gly Gly Gly Gly Gly Gly Ser Val Ala Ser Pro Thr
290                 295                 300

Ser Ser Ser Gly Ser Ser Ser Arg Gly Thr Glu Arg Pro Arg Ser Leu
305                 310                 315                 320

Lys Arg Gly Ser Lys Pro Ser Ala Ser Ser Ala Ser Leu Glu Lys Arg
                325                 330                 335

Met Lys Met Val Ser Gln Ser Phe Thr Gln Arg Phe Arg Leu Ser Arg
                340                 345                 350

Asp Arg Lys Val Ala Lys Ser Leu Ala Val Ile Val Ser Ile Phe Gly
                355                 360                 365

Leu Cys Trp Ala Pro Tyr Thr Leu Leu Met Ile Ile Arg Ala Ala Cys
370                 375                 380

His Gly His Cys Val Pro Asp Tyr Trp Tyr Glu Thr Ser Phe Trp Leu
385                 390                 395                 400

Leu Trp Ala Asn Ser Ala Val Asn Pro Val Leu Tyr Pro Leu Cys His
                405                 410                 415

His Ser Phe Arg Arg Ala Phe Thr Lys Leu Leu Cys Pro Gln Lys Leu
                420                 425                 430

Lys Ile Gln Pro His Ser Ser Leu Glu His Cys Trp Lys
                435                 440                 445

<210> SEQ ID NO 2
<211> LENGTH: 445
<212> TYPE: PRT
<213> ORGANISM: Monkey

<400> SEQUENCE: 2

Met Glu Arg Ala Pro Pro Asp Gly Pro Leu Asn Ala Ser Gly Ala Leu
1               5                  10                  15

Ala Gly Glu Ala Ala Ala Gly Gly Ala Arg Gly Phe Ser Ala Ala
            20                  25                  30

Trp Thr Ala Val Leu Ala Ala Leu Met Ala Leu Leu Ile Val Ala Thr
            35                  40                  45

Val Leu Gly Asn Ala Leu Val Met Leu Ala Phe Val Ala Asp Ser Ser
        50                  55                  60

Leu Arg Thr Gln Asn Asn Phe Phe Leu Leu Asn Leu Ala Ile Ser Asp
65                  70                  75                  80
```

```
Phe Leu Val Gly Ala Phe Cys Ile Pro Leu Tyr Val Pro Tyr Val Leu
                 85                  90                  95
Thr Gly Arg Trp Thr Phe Gly Arg Gly Leu Cys Lys Leu Trp Leu Val
            100                 105                 110
Val Asp Tyr Leu Leu Cys Thr Ser Ala Phe Asn Ile Val Leu Ile
        115                 120                 125
Ser Tyr Asp Arg Phe Leu Ser Val Thr Arg Ala Val Ser Tyr Arg Ala
    130                 135                 140
Gln Gln Gly Asn Thr Arg Arg Ala Val Arg Lys Met Leu Leu Val Trp
145                 150                 155                 160
Val Leu Ala Phe Leu Leu Tyr Gly Pro Ala Ile Leu Ser Trp Glu Tyr
                165                 170                 175
Leu Ser Gly Gly Ser Ser Ile Pro Glu Gly His Cys Tyr Ala Glu Phe
                180                 185                 190
Phe Tyr Asn Trp Tyr Phe Leu Ile Thr Ala Ser Thr Leu Glu Phe Phe
            195                 200                 205
Thr Pro Phe Leu Ser Val Thr Phe Phe Asn Leu Ser Ile Tyr Leu Asn
    210                 215                 220
Ile Gln Arg Arg Thr Arg Leu Arg Leu Asp Gly Ala Arg Glu Ala Gly
225                 230                 235                 240
Gly Pro Glu Pro Pro Glu Ala Gln Pro Ser Pro Pro Pro Pro Pro
                245                 250                 255
Gly Cys Trp Gly Cys Trp Gln Lys Gly His Gly Glu Ala Met Pro Leu
            260                 265                 270
His Arg Tyr Gly Val Gly Glu Ala Ala Ala Gly Ala Glu Ala Gly Glu
        275                 280                 285
Thr Ala Leu Gly Gly Gly Gly Gly Gly Ser Ala Ala Ser Pro Thr
    290                 295                 300
Ser Ser Ser Gly Ser Ser Ser Arg Gly Thr Glu Arg Pro Arg Ser Leu
305                 310                 315                 320
Lys Arg Gly Ser Lys Pro Ser Ala Ser Ser Ala Ser Leu Glu Lys Arg
                325                 330                 335
Met Lys Met Val Ser Gln Ser Phe Thr Gln Arg Phe Arg Leu Ser Arg
            340                 345                 350
Asp Arg Lys Val Ala Lys Ser Leu Ala Val Ile Val Ser Ile Phe Gly
        355                 360                 365
Leu Cys Trp Ala Pro Tyr Thr Leu Leu Met Ile Ile Arg Ala Ala Cys
    370                 375                 380
His Gly His Cys Val Pro Asp Tyr Trp Tyr Glu Thr Ser Phe Trp Leu
385                 390                 395                 400
Leu Trp Ala Asn Ser Ala Val Asn Pro Val Leu Tyr Pro Leu Cys His
                405                 410                 415
His Ser Phe Arg Arg Ala Phe Thr Lys Leu Leu Cys Pro Gln Lys Leu
            420                 425                 430
Lys Ile Gln Pro His Ser Ser Leu Glu Gln Cys Trp Lys
        435                 440                 445

<210> SEQ ID NO 3
<211> LENGTH: 445
<212> TYPE: PRT
<213> ORGANISM: Rat

<400> SEQUENCE: 3

Met Glu Arg Ala Pro Pro Asp Gly Leu Met Asn Ala Ser Gly Thr Leu
```

```
1               5                    10                   15
Ala Gly Glu Ala Ala Ala Gly Gly Ala Arg Gly Phe Ser Ala Ala
                20                  25                  30

Trp Thr Ala Val Leu Ala Ala Leu Met Ala Leu Leu Ile Val Ala Thr
        35                  40                  45

Val Leu Gly Asn Ala Leu Val Met Leu Ala Phe Val Ala Asp Ser Ser
    50                  55                  60

Leu Arg Thr Gln Asn Asn Phe Phe Leu Leu Asn Leu Ala Ile Ser Asp
65                  70                  75                  80

Phe Leu Val Gly Ala Phe Cys Ile Pro Leu Tyr Val Pro Tyr Val Leu
                85                  90                  95

Thr Gly Arg Trp Thr Phe Gly Arg Gly Leu Cys Lys Leu Trp Leu Val
                100                 105                 110

Val Asp Tyr Leu Leu Cys Ala Ser Ser Val Phe Asn Ile Val Leu Ile
            115                 120                 125

Ser Tyr Asp Arg Phe Leu Ser Val Thr Arg Ala Val Ser Tyr Arg Ala
            130                 135                 140

Gln Gln Gly Asp Thr Arg Arg Ala Val Arg Lys Met Ala Leu Val Trp
145                 150                 155                 160

Val Leu Ala Phe Leu Leu Tyr Gly Pro Ala Ile Leu Ser Trp Glu Tyr
                165                 170                 175

Leu Ser Gly Gly Ser Ser Ile Pro Glu Gly His Cys Tyr Ala Glu Phe
                180                 185                 190

Phe Tyr Asn Trp Tyr Phe Leu Ile Thr Ala Ser Thr Leu Glu Phe Phe
            195                 200                 205

Thr Pro Phe Leu Ser Val Thr Phe Phe Asn Leu Ser Ile Tyr Leu Asn
210                 215                 220

Ile Gln Arg Arg Thr Arg Leu Arg Leu Asp Gly Gly Arg Glu Ala Gly
225                 230                 235                 240

Pro Glu Pro Pro Pro Asp Ala Gln Pro Ser Pro Pro Ala Pro Pro
                245                 250                 255

Ser Cys Trp Gly Cys Trp Pro Lys Gly His Gly Glu Ala Met Pro Leu
            260                 265                 270

His Arg Tyr Gly Val Gly Glu Ala Gly Pro Gly Val Glu Ala Gly Glu
            275                 280                 285

Ala Ala Leu Gly Gly Gly Ser Gly Gly Gly Ala Ala Ala Ser Pro Thr
            290                 295                 300

Ser Ser Ser Gly Ser Ser Ser Arg Gly Thr Glu Arg Pro Arg Ser Leu
305                 310                 315                 320

Lys Arg Gly Ser Lys Pro Ser Ala Ser Ser Ala Ser Leu Glu Lys Arg
                325                 330                 335

Met Lys Met Val Ser Gln Ser Ile Thr Gln Arg Phe Arg Leu Ser Arg
            340                 345                 350

Asp Lys Lys Val Ala Lys Ser Leu Ala Ile Ile Val Ser Ile Phe Gly
            355                 360                 365

Leu Cys Trp Ala Pro Tyr Thr Leu Leu Met Ile Ile Arg Ala Ala Cys
    370                 375                 380

His Gly Arg Cys Ile Pro Asp Tyr Trp Tyr Glu Thr Ser Phe Trp Leu
385                 390                 395                 400

Leu Trp Ala Asn Ser Ala Val Asn Pro Val Leu Tyr Pro Leu Cys His
                405                 410                 415

Tyr Ser Phe Arg Arg Ala Phe Thr Lys Leu Leu Cys Pro Gln Lys Leu
            420                 425                 430
```

```
Lys Val Gln Pro His Gly Ser Leu Glu Gln Cys Trp Lys
    435                 440                 445
```